US011051948B2

(12) United States Patent
Arnold et al.

(10) Patent No.: US 11,051,948 B2
(45) Date of Patent: Jul. 6, 2021

(54) HINGE JOINT SYSTEM WITH DISTAL FEMORAL REPLACEMENT PROSTHETIC KNEE

(71) Applicant: Delta Ortho, LLC, Solana Beach, CA (US)

(72) Inventors: Benjamin Arnold, San Diego, CA (US); Brian Bowman, Carlsbad, CA (US); Diana Rosales, San Diego, CA (US); Paul Edwards, Little Rock, AR (US); C. Lowry Barnes, Little Rock, AR (US); Simon Mears, Little Rock, AR (US); Michael Neel, Memphis, TN (US); Daivon Deans, San Diego, CA (US); Jacob Hustedt, Solana Beach, CA (US); Jonathon Gold, Solana Beach, CA (US); Henry Warder, San Diego, CA (US); Brandon Duquesnel, Temecula, CA (US)

(73) Assignee: Delta Ortho, LLC, Solana Beach, CA (US)

( * ) Notice: Subject to any disclaimer, the term of this patent is extended or adjusted under 35 U.S.C. 154(b) by 56 days.

(21) Appl. No.: 16/399,762

(22) Filed: Apr. 30, 2019

(65) Prior Publication Data
US 2020/0060833 A1 Feb. 27, 2020

Related U.S. Application Data

(63) Continuation of application No. PCT/US2019/029735, filed on Apr. 29, 2019.
(Continued)

(51) Int. Cl.
A61F 2/38 (2006.01)
A61F 2/30 (2006.01)

(52) U.S. Cl.
CPC .......... A61F 2/3845 (2013.01); A61F 2/385 (2013.01); A61F 2/3868 (2013.01);
(Continued)

(58) Field of Classification Search
CPC ...... A61F 2/3836; A61F 2/384; A61F 2/3845; A61F 2/385; A61F 2/3868; A61F 2002/30624; A61F 2002/30632
See application file for complete search history.

(56) References Cited

U.S. PATENT DOCUMENTS 5,370,701 A   12/1994  Finn
5,620,415 A   4/1997   Lucey et al.
(Continued)

FOREIGN PATENT DOCUMENTS

WO   WO-2019210323 A1   10/2019

OTHER PUBLICATIONS

Search Report and Written Opinion for PCT/US19/029735 dated Jul. 12, 2019.

Primary Examiner — Brian A Dukert
(74) Attorney, Agent, or Firm — Acuity IP, LLC; Nathan S. Cassell

(57) ABSTRACT

Methods and systems are provided for a hinge knee system. A hinge knee system may comprise a femoral component; an insert; a tibial tray configured to be coupled to the insert; a tibial bushing configured to be disposed between the tibial tray and the insert; a poly locking screw configured to secure the tibial tray to the insert; a hinge box configured to be disposed between the femoral component and the insert; one or more cross-pin bushings configured to be disposed within the hinge box; a cross-pin configured to secure the hinge box to the femoral component; a hinge post configured to couple the hinge box to the tibial tray; and a hinge post set screw configured to secure the hinge box to the hinge post.

35 Claims, 37 Drawing Sheets

Related U.S. Application Data

(60) Provisional application No. 62/663,940, filed on Apr. 27, 2018.

(52) U.S. Cl.
CPC ............... *A61F 2002/30433* (2013.01); *A61F 2002/30624* (2013.01); *A61F 2002/30632* (2013.01); *A61F 2002/3863* (2013.01)

(56) References Cited

U.S. PATENT DOCUMENTS

| | | |
|---|---|---|
| 6,485,519 B2 * | 11/2002 | Meyers ................... A61F 2/385 623/20.14 |
| 7,572,292 B2 | 8/2009 | Crabtree et al. |
| 8,545,570 B2 | 10/2013 | Crabtree et al. |
| 2007/0129808 A1 | 6/2007 | Justin et al. |
| 2009/0125116 A1 | 5/2009 | Crabtree et al. |
| 2013/0190883 A1 | 7/2013 | Collard et al. |
| 2014/0114318 A1 | 4/2014 | May et al. |
| 2014/0236307 A1 * | 8/2014 | Whiteside ............... A61F 2/385 623/20.26 |
| 2016/0278938 A1 | 9/2016 | Goble et al. |
| 2017/0333197 A1 | 11/2017 | Roche et al. |

* cited by examiner

HINGE JOINT SYSTEM WITH DISTAL FEMORAL REPLACEMENT PROSTHETIC KNEE

CROSS-REFERENCE

This application is a continuation application of International Application No. PCT/US19/29735, filed on Apr. 29, 2019, which claims the benefit of U.S. Provisional Application No. 62/663,940, filed Apr. 27, 2018, entitled "HINGE JOINT SYSTEM WITH DISTAL FEMORAL REPLACEMENT PROSTHETIC KNEE", the entire contents of which are incorporated herein by reference.

BACKGROUND OF THE INVENTION

Field of the Invention

Reconstruction of the knee joint is treated with a total knee arthroplasty that is meant to replace the knee joint with metal and plastic components to replicate the kinematics of the knee joint. There exist numerous options for knee replacement devices, the choice of which to use is driven by patient anatomy, stability, deformity and intended functional use, but all systems include a femoral component, a tibial component, and an insert that acts as the bearing surface for the femoral component, along with other components as needed per the system used.

There are several major design options for knee replacement systems. Cruciate retaining systems leave the posterior cruciate ligament (PCL) in place, thereby naturally stabilizing the joint. Cruciate sacrificing systems require removal of the PCL but compensate with an implant that allows less free motion of the femoral component. One type of cruciate sacrificing system is a hinged knee system. Hinged knee systems are typically indicated for patients who have already had one or more total knee replacement surgeries, but, due to a wide range of possible factors, require a revision surgery with a new implant. Such factors may include bone necrosis, bi-condylar arthrosis caused by partly damaged collateral ligaments, previous implant wear, severe joint diseases with limitation of mobility due to degenerative, rheumatoid, or post traumatic arthrosis or arthritis, degradation of bone mass or inadequate amounts of bone mass, arthrosis of the patella flange, or varus/valgus deformities up to 30°. In addition to introducing a hinge mechanism to constrain knee motion and join the femur and tibia, hinged knee revision systems typically include longer intramedullary tibial and femoral stems and may include metal blocks (called "augments") that can be attached to the femoral and tibial components to replace degraded or missing bone.

The benefits of using hinged knees for revision surgeries are numerous: improved immediate post-operative mobility, decreased pain, and restored leg alignment through replacement of degraded bone. However, many current hinged knee systems do not allow surgeons to quickly switch between a non-hinged and hinged option intraoperatively, resulting in increased surgical working time and decreased surgical flexibility during revision procedures. Furthermore, the customizability of metal augments used in situations where distal femoral resections are required is currently very limited. In many cases, surgeons do not have the correctly sized augments needed to revise missing or degraded bone and are forced to compromise in other areas of the revision procedure—either by using a larger, bulkier femoral implant, or by selecting a longer stem. In some cases, the patient is instead referred to a trauma surgeon for the distal femoral fracture to be treated with bone plates, which have longer recovery times for the patient. Furthermore, current hinge knee systems are often overly complicated in their surgical technique and component design and are extremely expensive to utilize.

BACKGROUND ART

U.S. Pat. No. 8,545,570
U.S. Pat. No. 7,572,292

SUMMARY

An easy to use implant with intraoperative flexibility and many options for patient treatment of a joint replacement, including distal femoral fracture cases, is greatly desired. For example, a pre-assembled femoral component with the hinge components would decrease surgical room time from having to assemble them during the case. It also may make it easier for any surgeon familiar with primary and revision knee reconstruction surgeries to perform the hinge knee reconstruction since the hinged knee system would be very similar to a primary or revision surgical technique. It would also be desirable to have a hinge component of the assembly anteriorly accessible so as to reduce time in the surgical room by obviating the need to make additional resection(s) in order to access the lateral sides of the femur required by other hinge knee systems on the market. Additionally, it would be desirable to have various options for treating distal femoral fracture cases such that bone is completely replaced without the need for excessive resections or a switch to a total femur reconstruction system. Not necessarily all such aspects or advantages are achieved by any particular embodiment. Thus, various embodiments may be carried out in a manner that achieves or optimizes one advantage or group of advantages taught herein without necessarily achieving other aspects or advantages as may also be taught or suggested herein.

The present disclosure generally relates to knee replacement systems and more particularly relates to hinged knee systems and methods compatible with standard primary or revision surgical techniques and/or distal femoral replacement (DFR) procedures.

An aspect of the present disclosure provides a hinge knee system. The hinge knee system comprises a femoral component, an insert, a tibial tray, a hinge box, a hinge post, a hinge screw, a cross-pin, cross-pin bushings, tibial bushings, femoral augments, tibial augments, and stem extensions.

In some embodiments, the hinge knee system is a fixed hinge post design.

In some embodiments, the system can also treat DFR cases. The system may further comprise a DFR femoral augment and DFR augment screws. Alternatively, the femoral component may be a DFR femoral component. In some embodiments, the DFR femoral component may be pre-assembled to one or more hinge components (e.g., the hinge box, cross-pin, and cross-pin bushings) prior to surgical use. In some embodiments, the DFR system may further comprise a DFR stem. In some embodiments, one or more of the DFR system may allow for treatment of different distal femoral resection types. For example, the system may be configured to allow for intra-operative switching of components, such as switching from a resurfacing hinge to a DFR replacement.

In some embodiments, the system may comprise one or more components to limit hyperextension. For example, the femoral component may comprise a flat contour and the insert may comprise an anterior stop.

In some embodiments, the system may comprise one or more components configured to limit internal/external rotation. For example, the insert bearing surfaces may act as a primary rotation limiter and a tibial bushing may act as a secondary rotation limiter/stop.

In some embodiments, the femoral component may be pre-assembled to one or more hinge components (e.g., the hinge box, cross-pin, and cross-pin bushings) prior to surgical use.

In some embodiments, the hinge assembly may be an anterior hinge assembly. In some embodiments, the hinge assembly may comprise a hinge post, hinge box, and a hinge screw. The hinge post may be coupled to the hinge box with the hinge screw.

In some embodiments, the hinge post may be configured to lock to the femoral components to the tibial components. The hinge post may be configured to prevent excessive axial translation of the components. Alternatively, or in combination, the hinge post may be configured to reduce or prevent dislocation of the components.

In some embodiments, the hinge post may be configured to link the femoral components to the tibial components. The hinge post may, for example, be rotated from an unlocked position to a locked position in order to secure the femoral components to the tibial components.

In some embodiments, the hinge post assembly may be at least partially pre-assembled prior to surgery in order to facilitate surgical use.

Another aspect of the present disclosure provides a method for installing any of the hinge post knee systems described herein. The method may be substantially similar to other primary and revision systems on the market with the variation of a hinge post insertion and assembly step.

Another aspect of the present disclosure provides a hinged knee system with an anteriorly-assembled hinge that replicates the kinematics of the knee joint for indicated hinge knee or distal femoral replacement cases. A femoral component is pre-assembled with a hinge box, cross-pin, and bushings between its condylar surfaces. The femoral component comprises a femoral post configured to be coupled to a stem extension attachment(s) if needed. A tibial tray may comprise a post that can attach to stem extensions if needed. An aperture along the center of the tibial tray holds a bushing that acts as a bearing surface for the hinge post. The system further comprises an insert that connects to the tray and acts as a bearing surface for the femoral component. The hinge post may come in various lengths which correspond to different thicknesses of the insert available in the system. The hinge post assembly links the femoral components to the tibial components and is anteriorly secured in place in a hinge box. In an exemplary embodiment, the hinge pose assembly may be secured to the hinge box with a hinge screw. Additional femoral components may be included in the system to address distal femoral replacement cases.

Another aspect of the present disclosure provides a hinge knee system. The hinge knee system of this aspect comprises a femoral component; an insert; a tibial tray configured to be coupled to the insert; a tibial bushing configured to be disposed between the tibial tray and the insert; a poly locking screw configured to secure the tibial tray to the insert; a hinge box configured to be disposed between the femoral component and the insert; one or more cross-pin bushings configured to be disposed within the hinge box; a cross-pin configured to secure the hinge box to the femoral component; a hinge post configured to couple the hinge box to the tibial tray; and a hinge post set screw configured to secure the hinge box to the hinge post.

A further aspect of the present disclosures provides another hinge knee system. The hinge knee system of this aspect comprises a femoral component; a tibial component comprising an insert and a tibial tray; a hinge box coupled to the femoral component; and a hinge post configured to couple the hinge box to the tibial component.

Another aspect of the present disclosures provides an additional hinge knee system. The hinge knee system of this aspect comprises a femoral component; an insert; a tibial tray coupled to the insert with a poly locking screw; a tibial bushing disposed between the tibial tray and the insert; a hinge box disposed between the femoral component and the insert, wherein the hinge box comprises one or more cross-pin bushings disposed therein, wherein the hinge box is secured to the femoral component with a cross-pin; and a hinge post coupled to the hinge box and the tibial tray, wherein the hinge post is secured to the hinge box with a hinge post set screw.

Another aspect of the present disclosures provides a method of anteriorly assembling a hinge knee system. The method comprises resecting a tibia of a patient to correspond to a tibial component of a hinge knee system, the tibial component comprising a tibial tray and an insert. Additionally, the method comprises implanting the tibial component into the tibia of the patient. The method also comprises resecting a femur of the patient to correspond to a femoral component of the hinge knee system. Additionally, the method comprises implanting the femoral component into the femur of the patient. The method also comprises flexing the femoral component to expose a hinge box coupled to the femoral component. The method also comprises anteriorly assembling a hinge post through the hinge box into the insert. The method also comprises locking the hinge post to the tibial component. Additionally, the method comprises securing the hinge post to the hinge box.

A further aspect of the present disclosures provides a hinge instrument. The hinge instrument comprises a handle; a shaft body operably coupled to the handle; a turn-knob disposed on a proximal end of the handle; and an internal shaft rotatably disposed within the shaft body and operably coupled to the turn-knob, wherein a distal end of the shaft body is configured to install and lock a hinge post assembly to a femoral component and a tibial component of a hinge knee system, wherein a distal end of the internal shaft is configured to protrude past a distal end of the shaft body when the internal shaft is in a removal configuration, and wherein the distal end of the internal shaft is configured to correspond to a first aperture on a hinge post shaft of the hinge post assembly.

An additional aspect of the present disclosures provides a method of anteriorly removing a hinge knee system. The method comprises removing hinge post set screw from a hinge post and a hinge box of a hinge knee system. The method also comprises engaging a distal end of a shaft body of a hinge post instrument with a first aperture of a hinge post shaft of the hinge post. The method also comprises engaging a distal end of an internal shaft of the hinge post instrument with a second, threaded aperture of the hinge post shaft. The method also comprises rotating the hinge post shaft relative to a hinge post body of the hinge post with the hinge post instrument to unlock the hinge post shaft from a locked configuration. Additionally, the method comprises removing the hinge post from the hinge knee system.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
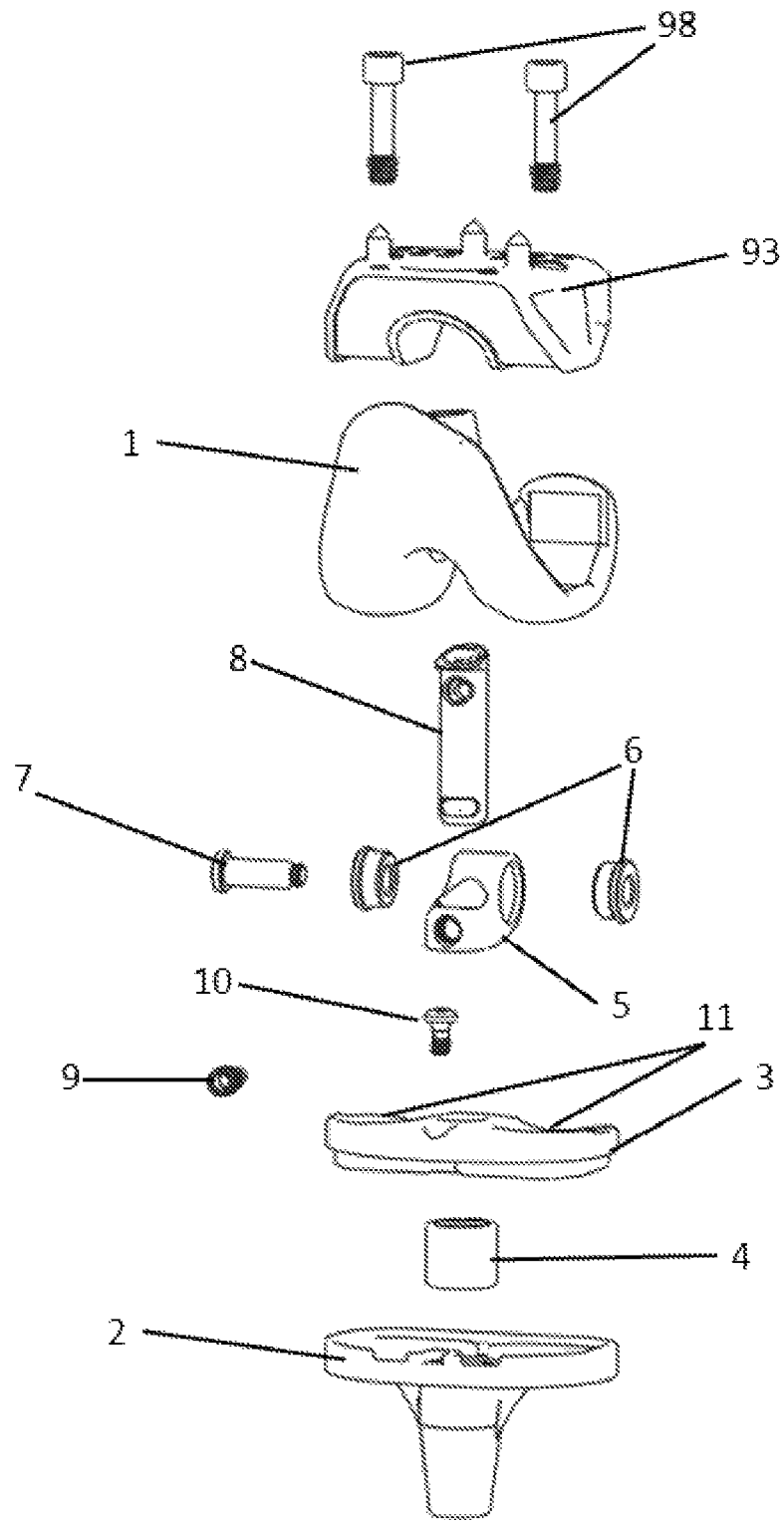
FIG. 1 is a perspective, exploded view of a hinge knee system, in accordance with embodiments.

In the following detailed description, reference is made to the accompanying figures, which form a part hereof. In the figures, similar symbols typically identify similar components, unless context dictates otherwise. The illustrative embodiments described in the detailed description, figures, and claims are not meant to be limiting. Other embodiments may be utilized, and other changes may be made, without departing from the scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

Although certain embodiments and examples are disclosed below, inventive subject matter extends beyond the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments, however, the order of description should not be construed to imply that these operations are order dependent. Additionally, the structures, systems, and/or devices described herein may be embodied as integrated components or as separate components.

For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Described herein are hinge knee systems and methods. The hinge knee systems described may be configured to be implanted in a similar manner to currently available primary and revision surgical technique and, as such, may be easier to use than other hinge knee systems available in the market.

During primary and revision surgical procedures, the tibia of the patient is resected and prepared with instrumentation matching the tibial implants (such as a tibial tray and tibial insert). The patient's femur is then resected to match the shape of the femoral component to be implanted. The intramedullary canal is then reamed to the appropriate length and diameter if a stem extension is required. If there is bone loss or additional resection is needed on the femur or tibia, femoral and tibial augments are provided that attach to the femoral component or the tibial tray. Before final implantation of the implants, trial parts are fit into the joint space to ensure appropriate knee kinematics are achieved with the chosen implant sizes.

Other hinge knee systems differ from the procedure described above in that there is additional hinge assembly required. There are various hinge designs on the market, but most require lateral assembly. One such example requires additional resection to access the lateral side of the femur. A hole is drilled through the femur to provide lateral access for a component, such as a pin, to affix the femoral component to the hinge or to the tibial components. Other hinge designs also vary in how they link the femoral components to the tibial components. Some designs use a free hinge post design, where the hinge post is free to move axially and the femoral components are not fixed in place, or a fixed hinge post design, where the femoral components are fixed to the tibial components to prevent dislocation.

To keep the surgical procedure of the hinge knee system described herein similar to primary knee replacement systems, as well as to reduce assembly time compared to other hinge knee systems, the hinge components, with the exception of the hinge post itself, may come pre-assembled to the femoral component prior to surgery. Pre-assembly of the hinge components may allow for anterior hinge assembly, which may remove the need for additional patient resection to access the lateral side of the knee compared to other hinge knee systems, thereby reducing surgical time and complexity and improving patient recovery. The femur, tibia, and intramedullary canal can then be prepped and resected in a similar fashion to primary and revision knee systems.

Additional femoral components may be included in the system for cases that require a distal femoral replacement (DFR). One or more DFR augments may be attached to the femoral component. The surgical procedure for DFR may be substantially similar to that described herein with the difference being that the distal femur is resected with a different resection guide for DFR cases.

In some embodiments, the system may have two separate configurations: a regular hinge knee configuration or a hinged distal femoral replacement knee configuration. The hinge knee system may be provided for use as a cemented configuration.

Also disclosed herein is a hinge knee system configured to treat DFR cases. The system comprises a DFR femoral component which may be substantially similar to other femoral components described herein and may be pre-assembled with all of the hinge components described herein except the hinge post. The hinge post may be assembled anterior during surgical implantation as described herein. The surgical procedure for DFR may be substantially similar to that described herein with the difference being that the distal femur is resected with a different resection guide for DFR cases The DFR embodiments described herein may allow for a quick and straightforward surgical implantation that not all systems in the market provide. A unique advantage of the systems described herein is that they allow distal femoral replacements to be treated with a hinge knee system, allowing non-trauma surgeons who are already familiar with primary and revision knees, to treat DFR cases.

FIG. 1 shows a perspective view of an exemplary hinge knee system in an exploded state. The system may comprise a femoral component 1, a tibial tray 2, an insert 3, a tibial bushing 4, a hinge box 5, two bushings 6, a cross-pin 7, a hinge post assembly 8, a hinge post set screw 9, and a poly locking screw 10. The system may further comprise a DFR augment 93 and DFR augment screws 98 as described herein. In some embodiments, one or more of the components shown (e.g., femoral component 1, a tibial tray 2, an insert 3, a tibial bushing 4, a hinge box 5, two bushings 6, a cross-pin 7, a hinge post assembly 8, a hinge post set screw 9, and a poly locking screw 10) may be optional and/or replaced by another component which performs a similar function. For example, hinge post set screw 9, which may be configured to couple the hinge post assembly 8 to hinge box 5, may be replaced by another component configured to couple the hinge post assembly 8 to hinge box 5 such as a pin, clip, latch, seal, or the like as will be understood to one of ordinary skill in the art based on the description herein.

In some embodiments, the femoral component 1 may be provided to the user pre-assembled with the hinge box 5, including the cross-pin 7 and bushings 6. Pre-assembly of the femoral component 1 with hinge box 5, cross-pin 7, and bushings 6 may facilitate anterior assembly of the hinge knee system as described herein. Alternatively, or in combination, pre-assembly of the femoral component 1 with hinge box 5, cross-pin 7, and bushings 6 may enhance the ease and/or speed of the surgical procedure, particularly compared to other hinge knee systems.

In other instances, intraoperative assembly by the user may be desired and the femoral component 1 may not be provided to the user pre-assembled with the hinge box 5, cross-pin 7, and bushings 6.

The system may be configured to allow for flexion and hyperextension similar to other systems on the market.

In some embodiments, the system may be configured to allow for about 0 degrees, about 1 degree, about 2 degrees, about 3 degrees, about 4 degrees, about 5 degrees, about 6 degrees, about 7 degrees, about 8 degrees, about 9 degrees, or about 10 degrees of hyperextension. The system may be configured to about for hyperextension within a range of about 0 degrees to about 10 degrees, about 2 degrees to about 8 degrees, about 3 degrees to about 7 degrees, or about 4 degrees to about 7 degrees. In a preferred embodiment, the system may be configured to allow for about 5 degrees of hyperextension.

In some embodiments, the system may be configured to allow for about 90 degrees, about 100 degrees, about 110 degrees, about 120 degrees, about 130 degrees, about 140 degrees, about 150 degrees, about 160 degrees, about 170 degrees, or about 180 degrees of flexion. The system may be configured to about for flexion of at least 90 degrees, about 100 degrees, about 110 degrees, about 120 degrees, about 130 degrees, about 140 degrees, about 150 degrees, about 160 degrees, about 170 degrees, or about 180 degrees. In a preferred embodiment, the system may be configured to allow for a minimum of about 120 degrees of flexion.

The system may be configured to allow for internal/external rotation similar to other systems in the art. For example, a bearing surface 11 of the insert 3 may be configured to dictate internal/external rotation as described herein. The system may, for example, be configured to allow for a minimum of about 15 degrees of rotation in each direction to allow for key knee kinematics. The system may be configured to allow for at least about 10 degrees, about 15 degrees, about 20 degrees, about 25 degrees, about 30 degrees, about 35 degrees, about 40 degrees, about 45 degrees, about 50 degrees, about 55 degrees, about 60 degrees, about 65 degrees, about 70 degrees, about 75 degrees, about 80 degrees, about 85 degrees, or about 90 degrees of internal/external rotation in each direction.

One or more components of the system may comprise more than one size option, thus enabling the surgeon to select the correctly sized component prior to or during surgery to suit the needs of the patient.

Figure 2A:
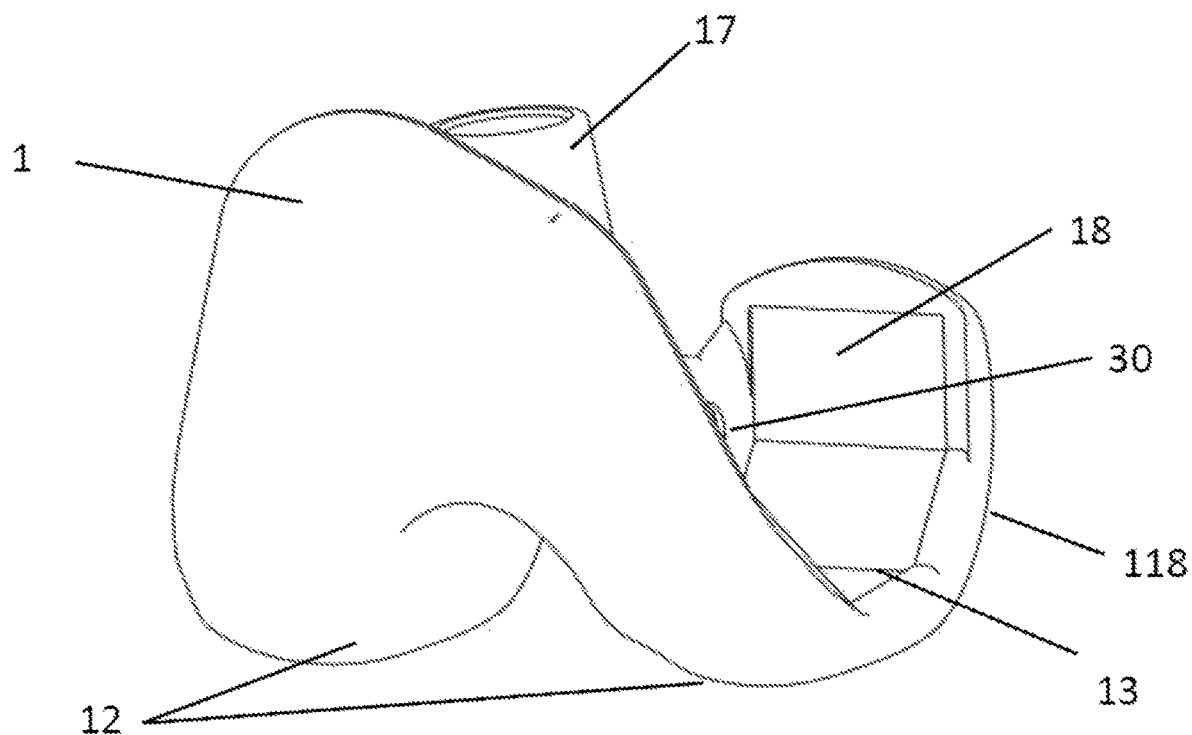
FIG. 2a is a perspective view of a femoral component, in accordance with embodiments.
Figure 2B:
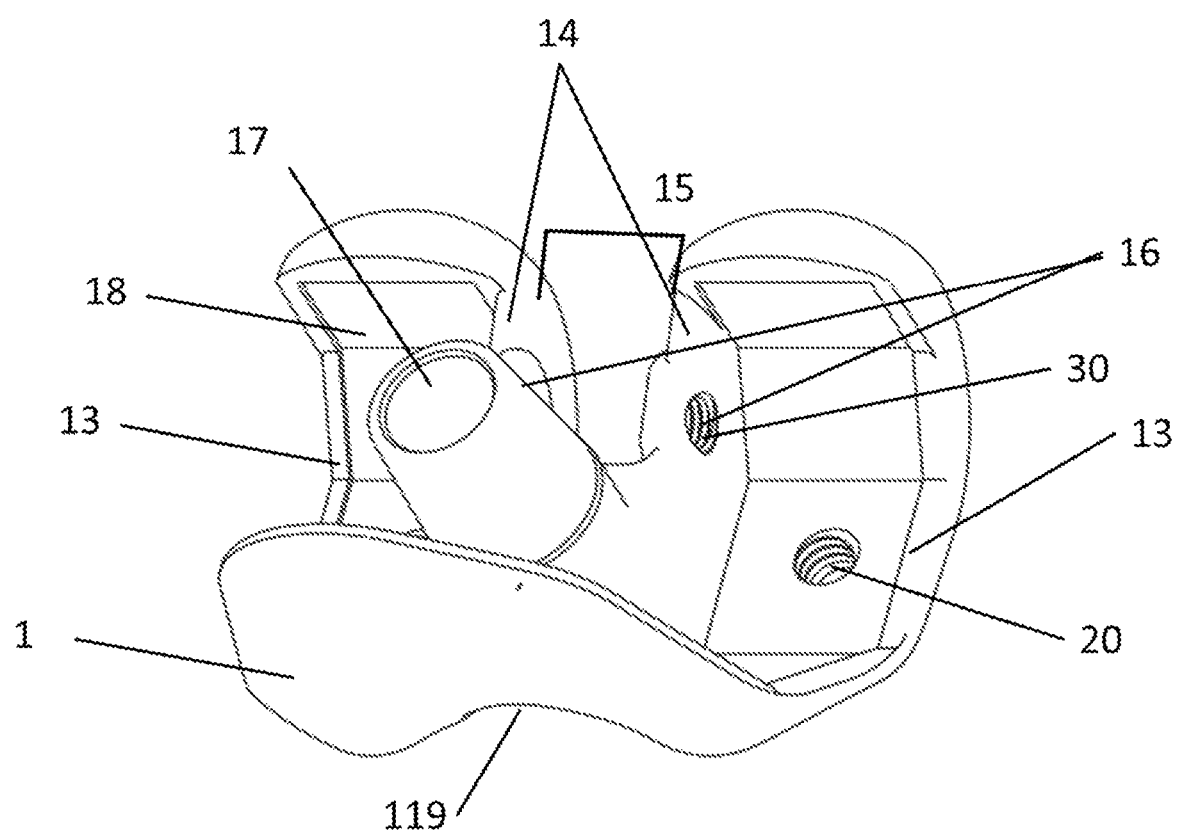
FIG. 2b is a proximal perspective view of the femoral component of FIG. 2b, in accordance with embodiments.
Figure 5:
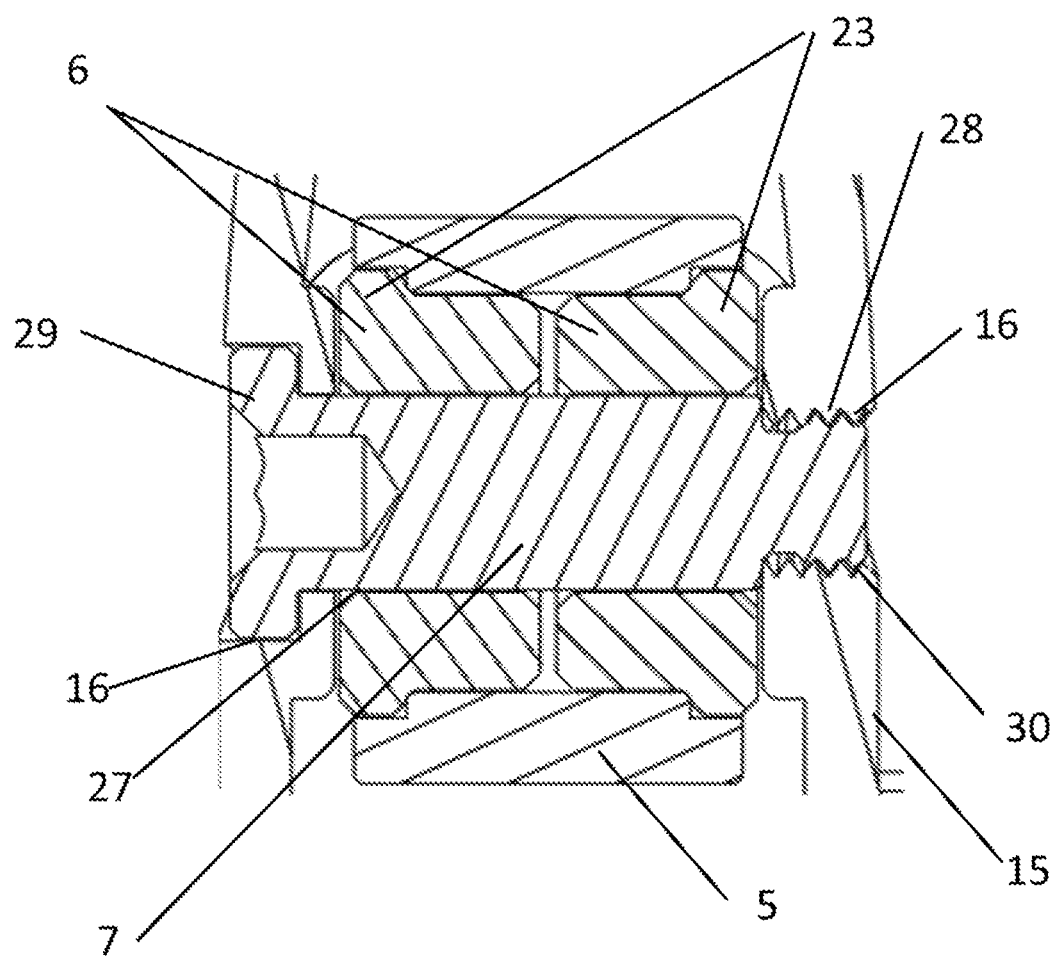
FIG. 5 is an anterior cross-section view of the pre-assembled hinge components in the femoral component of FIG. 3b taken on a plane that lies on the axis of a cross-pin, in accordance with embodiments.

FIG. 2a shows a perspective view of a femoral component 1. FIG. 2b shows a proximal perspective view of the femoral component 1. The femoral component 1 may comprise two highly polished, spherically-shaped condylar bearing surfaces 12, which may be similar to those common in the market. A proximal surface 13 of the condylar bearing surfaces 12 may be shaped to correspond to cuts made on the femur during surgery with a femoral cutting guide similar to others on the market. One or more cut outs 18 on the same proximal surfaces 13 of the femoral component 1 may provide space for a biocompatible bone cement to be placed for fixation of the femoral component 1 to the bone. The cement cut-outs 18 may also provide space for one or more femoral augments (e.g., femoral augments 90 shown in FIG. 23) to be placed on the proximal surface of the femoral component 1. The femoral augments can be fixed to the femoral component with screws, bone cement, or the like as described herein. One or more threaded apertures 20 in the proximal surface of the femoral component 1 may be disposed on either side of the intercondylar box 15 and allow for the femoral augment(s) to be fixed to the femoral component 1. Walls 14 between the condylar bearing surfaces 12 may form an intercondylar box 15. The intercondylar box 15 space may be configured to house a hinge box (e.g., hinge box 5 shown in FIG. 1), one or more bushings (e.g., two bushings 6 shown in FIG. 1), and a securing mechanism (e.g., cross-pin 7 shown in FIG. 1), all of which may come pre-assembled to the femoral component as shown in FIG. 5. A small aperture 16 on each wall of the box 15 may be provided for the cross-pin 7 to affix the hinge components to the femoral component 1. In some embodiments, the aperture 16 on the medial wall of the intercondylar box 15 may be threaded 30 as described herein. The femoral component 1 may further comprise a femoral stem 17 on the proximal end of the intercondylar box 15 configured to connect one or more optional stem extensions (e.g., stem extension 112 shown in FIG. 13) as described herein. The stem extensions could be affixed to the femoral component 1 with a taper, a screw, or the like, or any combination thereof as will be understood by one of ordinary skill in the art based on the teachings herein.

In some embodiments, the femoral component 1 may be a one-piece construction. In some embodiments, the femoral component 1 may comprise a multi-part construction.

The femoral component 1 may come in different sizes to accommodate varying patient anatomy. For example, the system may be configured to provide five differently-sized femoral components 1 similar to the size ranges and options of other systems in the market.

In some embodiments, the medial-lateral dimension of the femoral component 1 may be within a range of about 51 mm to about 80 mm. In some embodiments, the anterior-posterior dimension of the femoral component 1 may be within a range of about 50 mm to about 74 mm. It will be understood by one of ordinary skill in the art that the dimensions and size of the femoral component 1 may be selected on a patient by patient basis in order to most closely match the previously-existing patient anatomy.

The inter-condylar box 15 width may be configured for each femoral component 1 size offered in the system. For example, the inter-condylar box 15 may comprise a width within a range of about 14 mm to about 22 mm.

The femoral component 1 may comprise any appropriate biocompatible metal similar to other systems in the art. For example, the femoral component 1 may comprise cobalt chromium, titanium, titanium-based alloys, stainless steel, or the like, or any combination thereof.

Figure 3A:
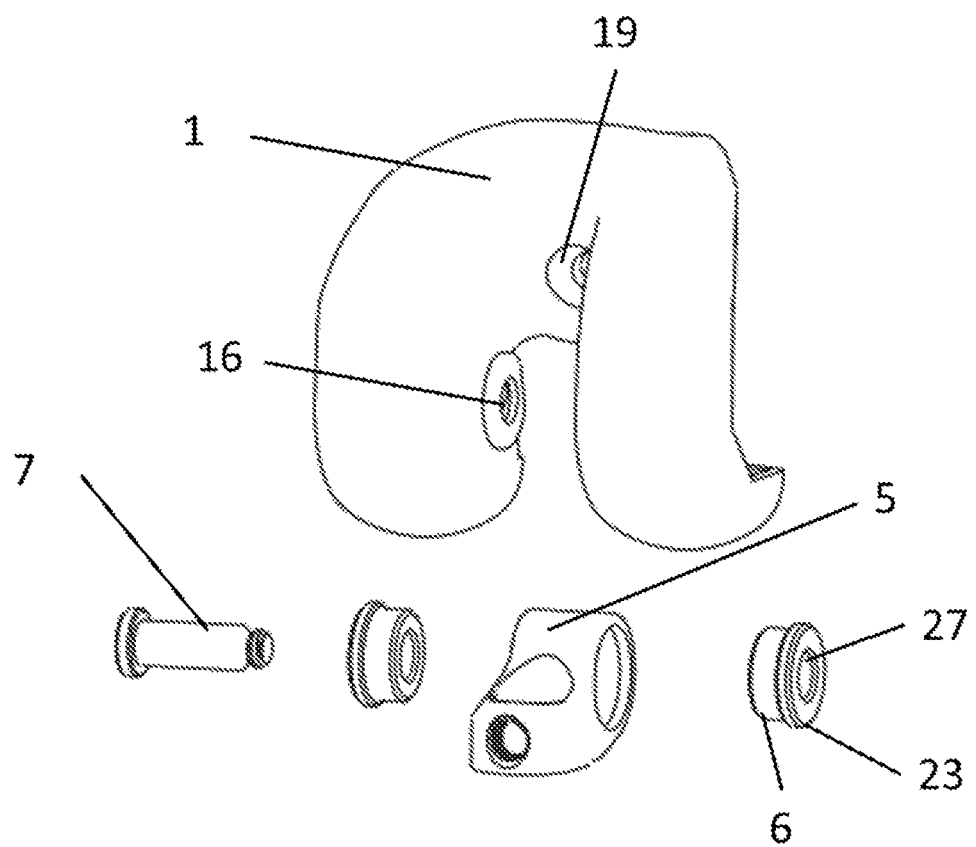
FIG. 3a is a perspective, exploded view of hinge components that may be pre-assembled into the femoral component with an optional cross-pin, in accordance with embodiments.
Figure 3B:
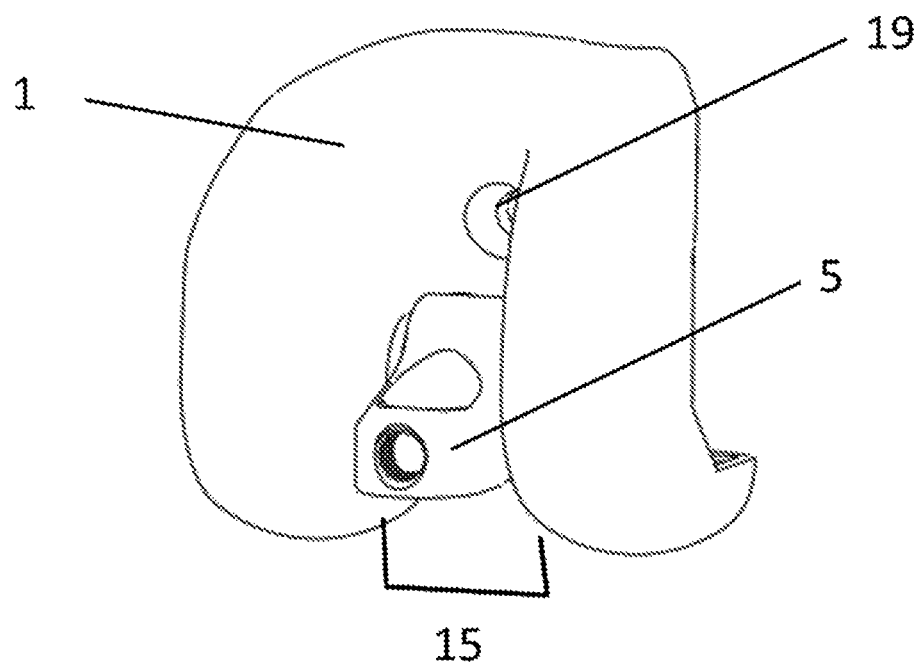
FIG. 3b is a perspective view of a pre-assembled femoral component with a hinge box, bushings, and cross-pin in place, in accordance with embodiments.

FIG. 3a shows a perspective, exploded view of hinge components that may be pre-assembled into the femoral component 1 with an optional cross-pin 7. FIG. 3b shows a perspective view of a pre-assembled femoral component 1 with a hinge box 5, bushings 6, and cross-pin 7 in place. The distal end of the femoral component 1 is shown in FIGS. 3a and 3b. An aperture 19 may be disposed within the inter-condylar box 15. The aperture 19 may be configured to enable a screw or other attachment mechanism to secure a femoral stem (e.g., femoral stem 17 shown in FIGS. 2a and 2b) to the femoral component 1. Aperture 16 may be disposed on each wall of the intercondylar box 15 for the cross-pin 7 to affix the hinge components to the femoral component 1. Each bushing may comprise a head 23 and an aperture 27. The head 23 may be configured to limit the insertion depth of the cross-pin 7 into the hinge box 5. For example, head 23 may be configured to fit into a countersink of the hinge box 5 (such as posterior countersink 22 as shown in FIG. 5). The aperture 27 through the center of each bushing 6 may be configured such that the inner walls of the aperture 27 act as a bearing surface for the cross-pin 7.

The bushings 6 may comprise an appropriate biocompatible material similar to other systems in the art. The bushings 6 may comprise an appropriate biocompatible plastic. For example, the bushings 6 may comprise ultra high molecular weight polyethylene (UHMWPE), ultra high cross-linked polyethylene (UHXLPE), vitamin E-doped UHMWPE, polytetrafluoroethylene (PTFE), low density polyethylene (LDPE), high density polyethylene (PEHD), polysulfone, polyetheretherketone (PEEK), polypropylene (PP), or the like, or any combination thereof.

In some embodiments, the bushings 6 are identical. In some embodiments, the bushings 6 have the same shape. In some embodiments, the bushings 6 are made of the same material(s).

In some embodiments, the bushings 6 are different. In some embodiments, one or more bushing 6 may have a different shape that one or more other bushing 6. In some embodiments, one or more of the bushings 6 may be made of a different material(s).

Figure 4:
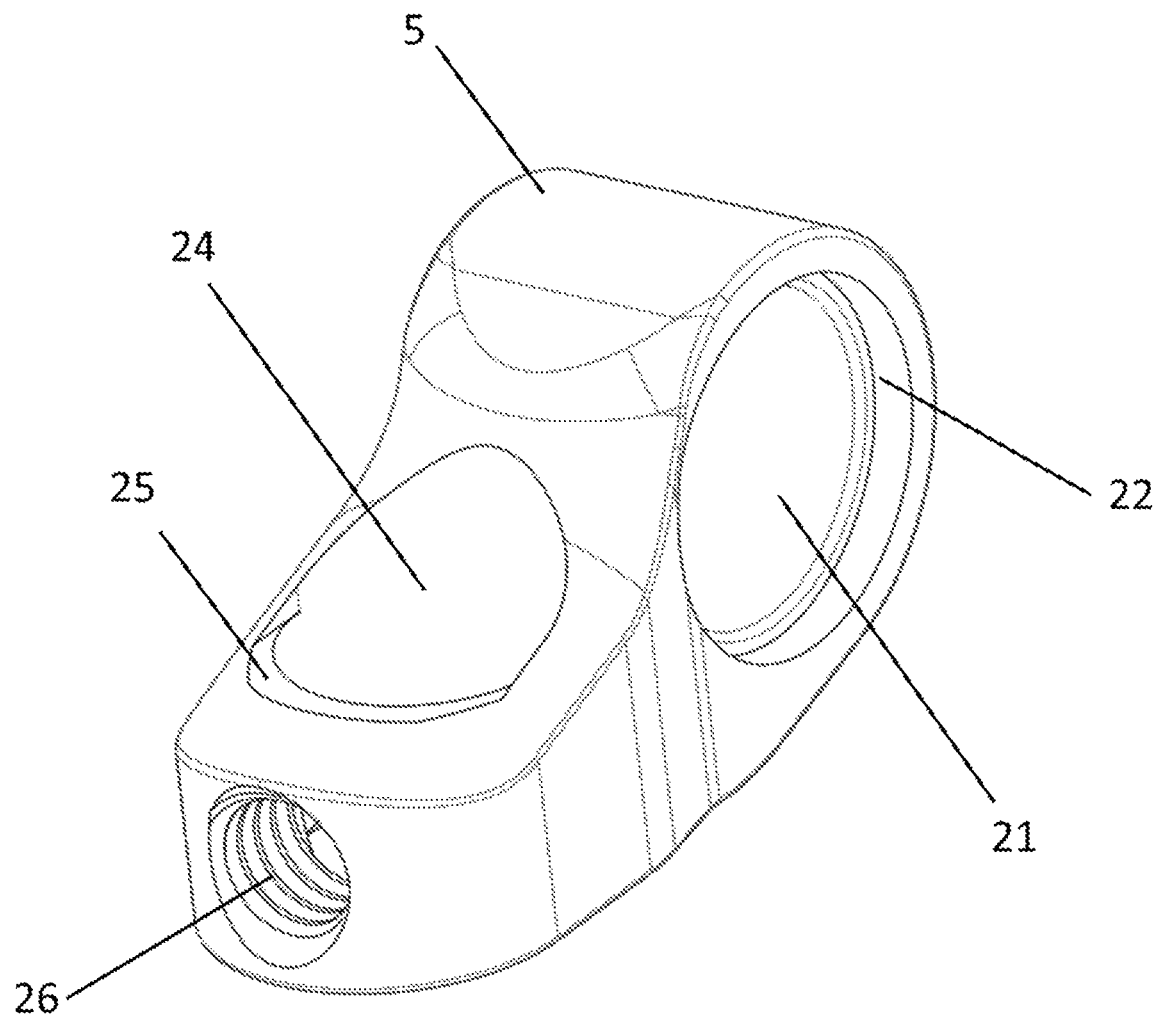
FIG. 4 is a perspective view of a hinge box, in accordance with embodiments.
Figure 13:
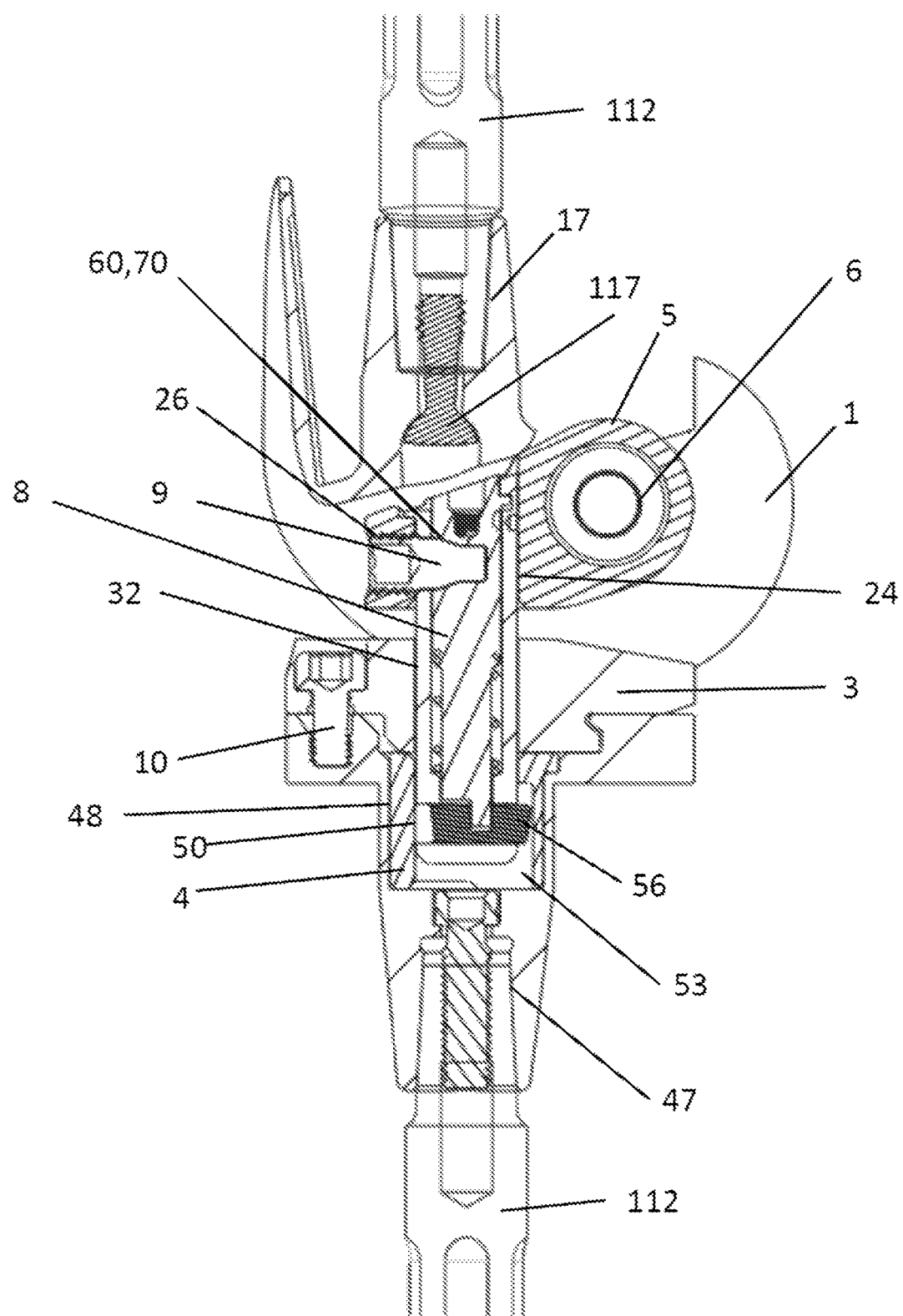
FIG. 13 is a cross-sectional view of the assembled system of FIG. 1 (excluding DFR augment and screws) with the hinge post fully engaged within the tibial bushing and locked in place with the hinge post set screw, in accordance with embodiments.

FIG. 4 shows a perspective view of a hinge box 5. The hinge box 5 may comprise a through hole 21 on the posterior end which may be shaped to correspond to the outer perimeter of the bushings 6. During assembly, a bushing 6 may be inserted into the through hole 21 as shown in FIG. 5. Countersinks 22 on each end of the through hole 21 may be shaped to correspond to the head 23 of the bushings 6 (shown in FIG. 3a) and act as a stop to correctly position the bushings 6 within the through hole 21. Towards an anterior end of the hinge box 5, a hinge post through hole 24 may be disposed. The hinge post through hole 24 may be configured to accept a hinge post assembly (e.g., hinge post assembly 8 shown in FIG. 1) therein. A countersink region 25 on the through hole 24 may be configured to correspond to one or more features on the hinge post assembly 8 (e.g. the proximal head 59 of the hinge post body 54 shown in FIG. 16) so that the hinge post assembly 8 sits inside the hinge box 5 and does not fall through when assembled as shown in FIG. 3a. For example, the hinge post assembly 8 may sit flush within the hinge box 5. The anterior surface of the hinge box 5 may comprise a small aperture 26 configured to align with one or more apertures on the hinge post assembly 8 (e.g., apertures 60, 70 shown in FIGS. 16-17b) in order to provide access for a hinge screw (e.g., hinge screw 9 shown in FIG. 13) to affix the hinge post assembly 8 to the hinge box 5 (e.g., as shown in FIG. 13).

The overall shape of the hinge box 5 may be optimized to (a) fit within the inter-condylar box 15 of the femoral component 1 and/or (b) to have enough space therewithin to house the bushings 6 and hinge post assembly 8 as described herein.

The shape of the hinge box 5 may be configured to accommodate the fixed dimensions of the bushings 6 and the hinge post assembly 8. The hinge post assembly 8 and cross-pin 7 diameter dimension may be defined such that they are no smaller than similar features in other systems in the art. The hinge post assembly 8 and cross-pin 7 diameter dimension may be defined such that they can withstand physiologic loading conditions a patient may experience during use.

The center of the hinge post through hole 24 may be aligned with the center of a tibial post (e.g., tibial post 45 shown in FIGS. 11a and 11b) on the tibial tray 2 such that it allows for the hinge post assembly 8 to fit through and into the tibial bushing 4, which sits within the tibial post 45.

The posterior through hole 21 may be configured to align on a posterior location on the femoral component 1 that allows for the best knee kinematics for the system. Due to the nature of the single radius design of the condylar bearing surfaces 12 of the hinged knee system described herein, the posterior through hole 21 may be placed at the center of the arc that defines the single radius condylar bearing surfaces 12. The posterior through hole 21 may not be placed too anteriorly in order to avoid it impinging with the hinge post through hole 24.

The size of the hinge box 5 may be configured to correspond to the size of the inter-condylar box 15. The system may be configured such that there exists a hinge box 5 size that corresponds to each sized femoral component 1. The width of the hinge boxes 5 may be within a range of about 14 mm to about 21 mm such that they fit within the inter-condylar box 15 of each corresponding femoral component 1 as described herein.

The hinge box 5 may comprise an appropriate biocompatible metal similar to other systems in the art. For example, the hinge box 5 may comprise cobalt chromium, titanium, titanium-based alloys, stainless steel, or the like, or any combination thereof.

The hinge post through hole 24 may be sized and shaped to correspond to an outer dimension of the hinge post assembly 8. For example, in a preferred embodiment, the hinge post through hole 24 and the hinge post assembly 8 may each comprise a circular cross-section in order to allow for axial rotation of the components. In some embodiments, the hinge post through hole 24 and the hinge post assembly 8 may each comprise a cross-sectional shape configured to allow for about 15 degrees of axial rotation in each direction as described herein.

FIG. 5 shows an anterior cross-sectional view of the hinge components pre-assembled to the femoral component 1. The bushings 6 are configured to be advanced into the horizontal aperture 21 of the hinge box 5 on both sides. Each bushing 6 may comprise a head 23 that fits into the posterior countersink 22 of the hinge box 5 as described herein. With the bushings 6 in place, the hinge box 5 may be placed within the inter-condylar box 15 of the femoral component 1 such that the apertures 27 of the bushings 6 and the aperture 16 of the inter-condylar box 15 are aligned. The cross-pin 7 may then be inserted through the aperture 16 in the lateral wall of the inter-condylar box 15, through the aperture 27 of bushings 6, and fixed in place on the opposite wall of the inter-condylar box 15.

The cross-pin 7 may comprise be a singular part construction. Alternatively, the cross-pin 7 may be a multi-part construction.

The cross-pin 7 may comprise an appropriate biocompatible metal. For example, the cross-pin 7 may comprise cobalt chromium, titanium, titanium-based alloys, stainless steel, or the like, or any combination thereof.

There are various ways the cross-pin 7 can be fixed in place. For example, the cross-pin 7 and the aperture 16 may be correspondingly threaded to enable the cross-pin 7 to be screwed into the aperture 16. Alternatively, or in combination, the cross-pin 7 may comprise one or more features configured to engage with the aperture 16 with a snap-fit such that the cross-pin 7 snaps into the aperture 16 to secure it in place.

In a preferred embodiment, the cross-pin 7 may comprise threads on its distal end 28 and a screw head on the proximal end 29 configured to correspond to a hex or torx driver or the like. The aperture 16 on the medial wall of the inter-condylar box 15 may be correspondingly threaded 30. The cross-pin 7 can then be screwed into place with the appropriate driver.

Because the inter-condylar box 15 size may differ for each differently-sized femoral component 1 as described herein, the hinge box 5 and cross-pin 7 may be similarly sized to correspond to each differently-side femoral component 1. The cross-pin 7 may, for example, comprise a length which matches the width of the inter-condylar box 15. In some embodiments, the cross-pin 7 may comprise a length within a range of about 14 mm to about 22 mm.

In many embodiments, the femoral component 1 and the hinge components may be pre-assembled prior to surgical use. This may be beneficial in that it may enable a surgeon, or anyone in the surgical room, to select the correct femoral component 1 without worrying about choosing the correct sizing of the various other hinge components, as the assembly described could be completed during manufacturing and thus be ready for use during surgery.

Figure 6A:
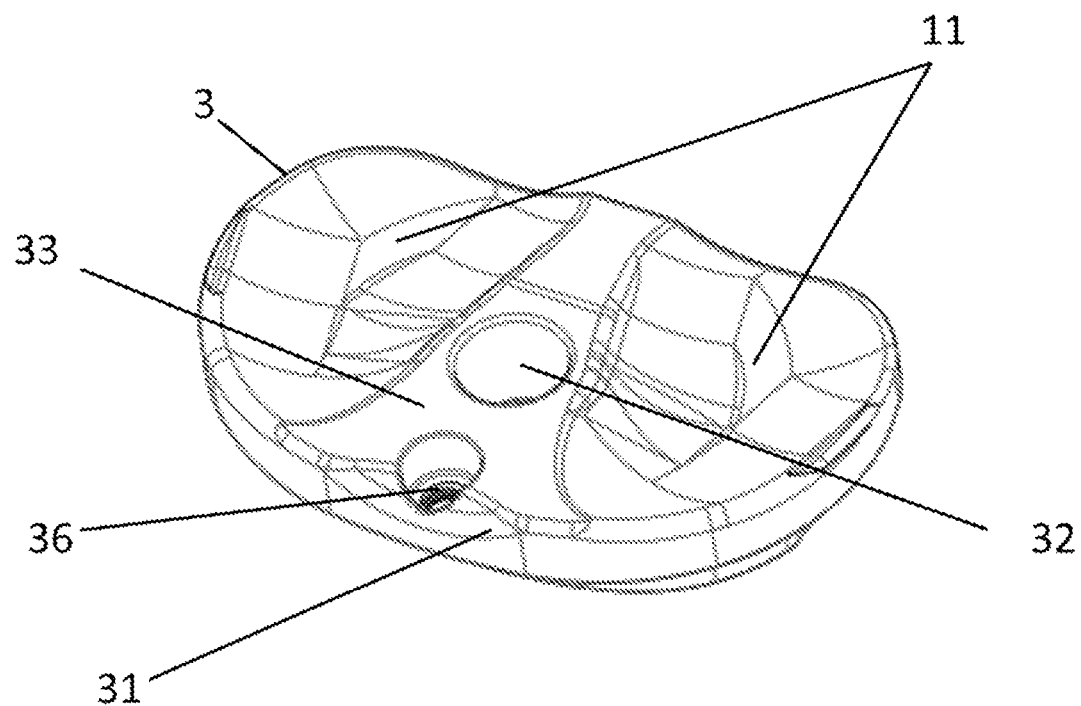
FIG. 6a is a perspective view of an insert comprising a locking feature on the proximal anterior surface, in accordance with embodiments.
Figure 6B:
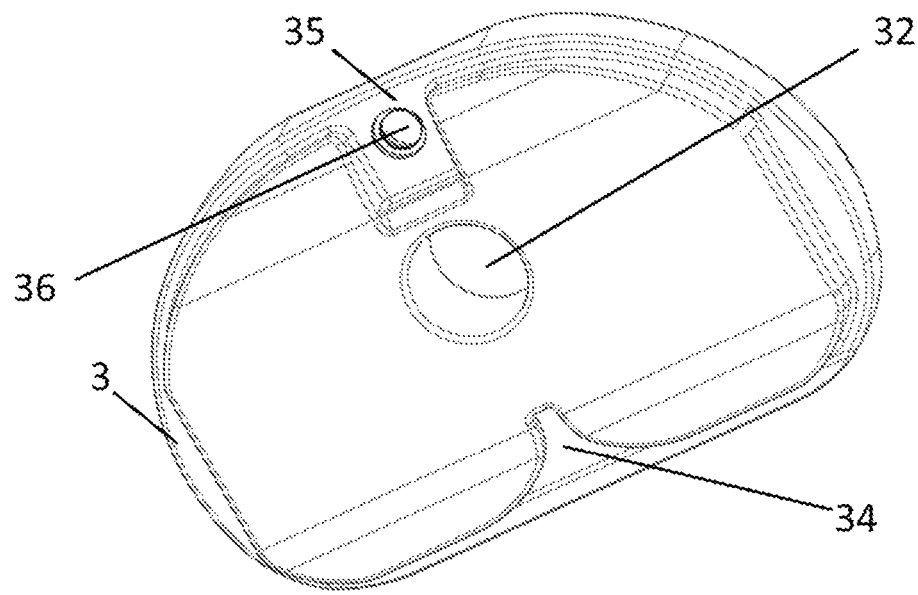
FIG. 6b is a distal surface perspective view of an insert comprising locking features that engage with a tibial tray, in accordance with embodiments.

FIG. 6a shows a perspective view of a proximal anterior surface of an insert 3 comprising a locking feature 36 on the proximal anterior surface. FIG. 6b shows a perspective view of a distal surface of the insert 3 comprising locking features 34, 36 configured to engage with a tibial tray (e.g., tibial tray 2 as shown in FIG. 7b). The proximal surface of the insert 3 may act as a bearing surface for the condylar bearing surfaces 12 of the femoral component 1. The proximal surface of the insert 3 may be configured with condylar surface grooves 11 configured to guide the motion of the knee similar to other systems in the market. The condylar surface grooves 11 may be configured such that they correspond to the condylar bearing surfaces 12 of the femoral component 1 and dictate motion of the system as described herein. The anterior portion of the insert 3 may be configured to guide the motion of the patella with a centrally-located patellar groove 31, similar to others on the market, which may provide space for and help guide the movement of the patella. The insert 3 may comprise a hinge post aperture 32 through its center that may be aligned with the center of the tibial bushing 4 as shown in FIG. 13. A flat, cleared space 33 may be disposed in the center of the insert 3 in order to constrain internal/external rotation motion to a desired extent and provide space for the hinge box 5 to fit thereover. As shown in FIG. 13, there may be a space between the distal surface of the hinge box 5 and the proximal surface of the insert 3 which may be configured to account for possible wear of the insert 3 so there is little or no impingement between the hinge box 5 and the insert 3.

The distal surface of the insert 3 may comprise one or more features configured to interact with a tibial tray (e.g., tibial tray 2 as shown in FIG. 13) so as to couple the two components to one another. Connection techniques known in the art can be used to join the tibial tray and the insert 3 to one another. For example, the tibial tray and the insert 3 may be coupled to one another with a screw, a pin, or the like. In a preferred embodiment, as shown in FIGS. 6b and 7b, the connection method may comprise two parts: a posterior portion 34 comprising an undercut similar to known art in the market and an anterior portion 35 that includes the use of a poly lock screw 10.

The flat, cleared space 33 may be configured to constrain internal/external rotational motion to a pre-determined extent. The hinge knee system may vary from having no rotational stop to allowing for any degree of rotation desired, similar to other hinge knee systems. When the system comprises a rotational stop as described herein, the system may provide for internal/external rotation within a range of about 0 degrees to about 15 degrees or more. In a preferred embodiments, the system may be configured to allow for a minimum of 15 degrees of internal/external rotation.

The insert 3 may comprise a symmetric component. The proximal surface 11 of the insert 3 may comprise at least one axis of symmetry. Alternatively, or in combination, the distal surface of the insert 3 may comprise at least one axis of symmetry.

The insert 3 may comprise varying thicknesses. The insert 3 may comprise a thickness within a range of about 9 mm to about 20 mm.

The insert 3 may come in varying sizes configured to match a size of the tibial tray (e.g., tibial tray 2). Each tibial tray size described herein may have a correspondingly shaped and sized insert 3. For example, if five tibial tray sizes are provided, then five insert 3 sizes may also be provided. The outside profile of the insert 3 may be shaped to match the profile of the tibial tray base (e.g., tibial tray base 44 shown in FIG. 11b) such that they are line-to-line and there is no over-hang between the components.

The insert 3 may comprise an appropriate biocompatible material similar to other systems in the art. The insert 3 may comprise an appropriate biocompatible plastic. For example, the insert 3 may comprise UHMWPE or UHXLPE.

Figure 7A:
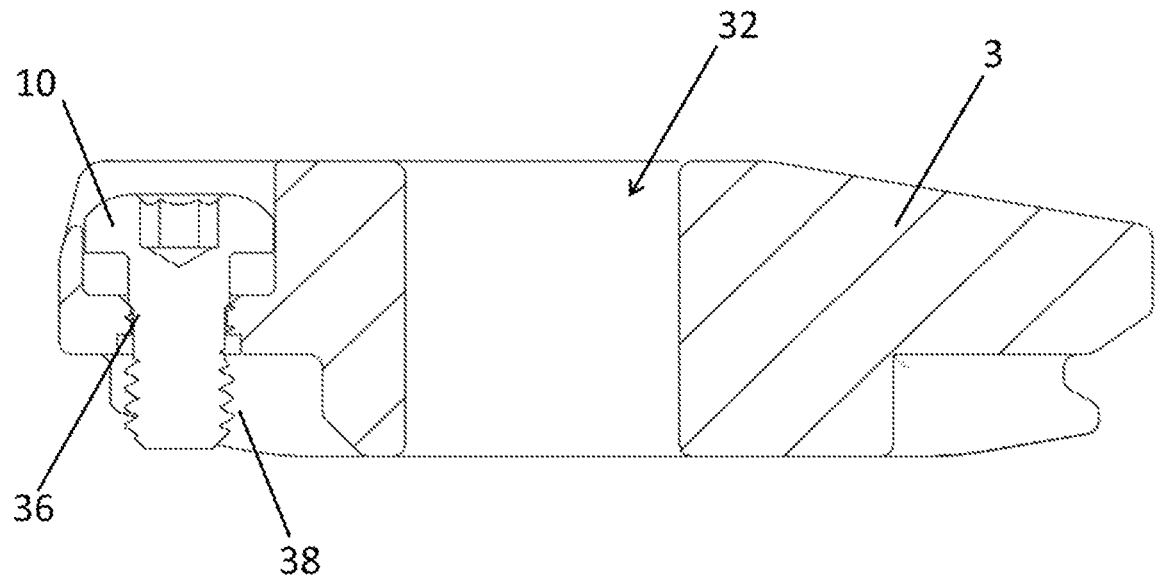
FIG. 7a is a lateral cross-sectional view of a self-retained assembly that includes a poly lock screw and insert, in accordance with embodiments.
Figure 7B:
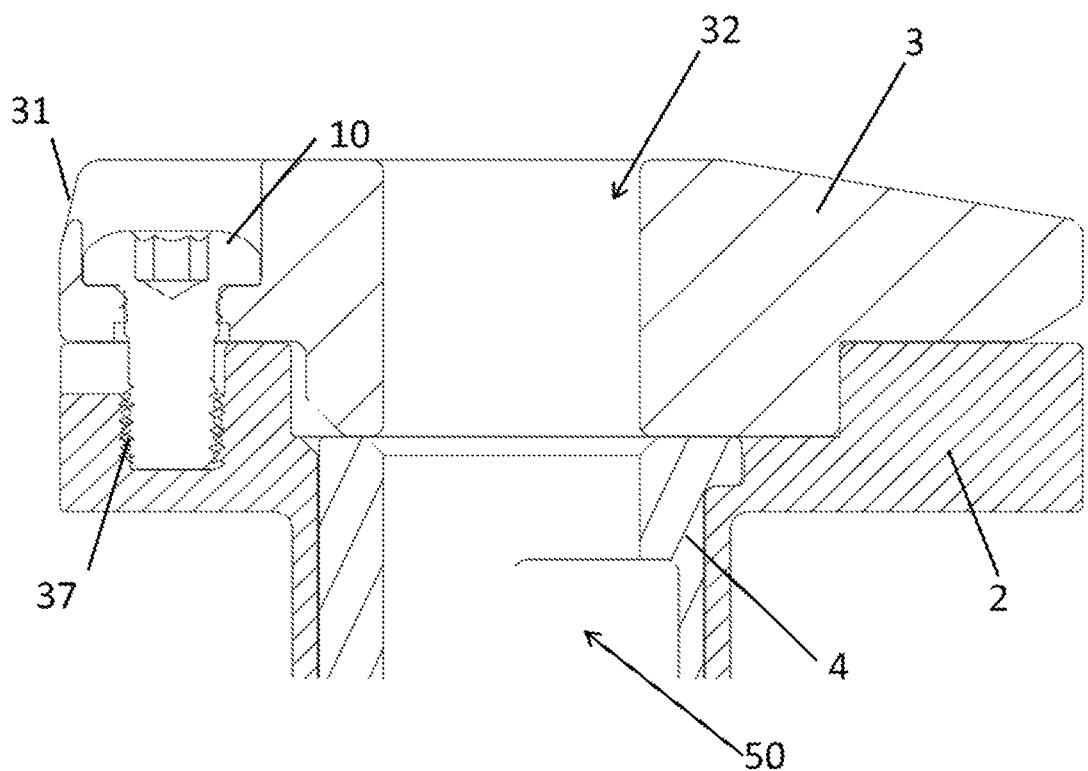
FIG. 7b is a lateral cross-sectional view of an anterior locking assembly between a tray, insert, and poly lock screw, in accordance with embodiments.

FIG. 7a shows a lateral cross-sectional view of a self-retained assembly that includes a poly lock screw 10 and an insert 3. FIG. 7b shows a lateral cross-sectional view of an anterior locking assembly between a tibial tray 2, insert 3, and poly lock screw 10. The poly lock screw 10 may be assembled into the anterior aperture 36 on the insert 3 prior to packaging such that it is self-retained in the insert 3. By pre-assembling the poly lock screw 10 into the anterior aperture 36 on the insert 3, the number of components being handled, and the number of components which may be dropped, during a case may be reduced or minimized.

The poly lock screw 10 may be retained within the insert 3 in various ways as described herein. In a preferred embodiment, the poly lock screw 10 may be retained in the insert 3 via threads in the anterior aperture 36. After the poly lock screw 10 is threaded into the anterior aperture 36, the poly lock screw 10 may be held in place by interference between the diameter of the threaded aperture 36 and the slightly larger diameter of the poly lock screw 10. The assembly of the poly lock screw 10 to the insert 3 may be done during the manufacturing and assembly processes such that the two components can be packaged together and ready for use during surgery. In the example embodiment described for locking between the tibial tray 2 and the insert 3, the insert 3 may be slid onto the tibial tray 2 during surgery. It will be understood by one of ordinary skill in the art that other coupling methods may be used as desired and may be guided by at least in part the choice of locking mechanism. After the insert 3 is placed onto the tibial tray 2 during the case, it may then be impacted so it is fully seated in the tibial tray 2 as shown in FIG. 7b. Finally, a driver may be used to push down and/or thread the poly lock screw 10 into the threaded aperture 37 of the tibial tray 2 in order to secure the tibial tray 2 to the insert 3. The final locked position between the insert 3, the poly lock screw 10, and the tibial tray 2 is shown in FIG. 7b.

Figure 8:
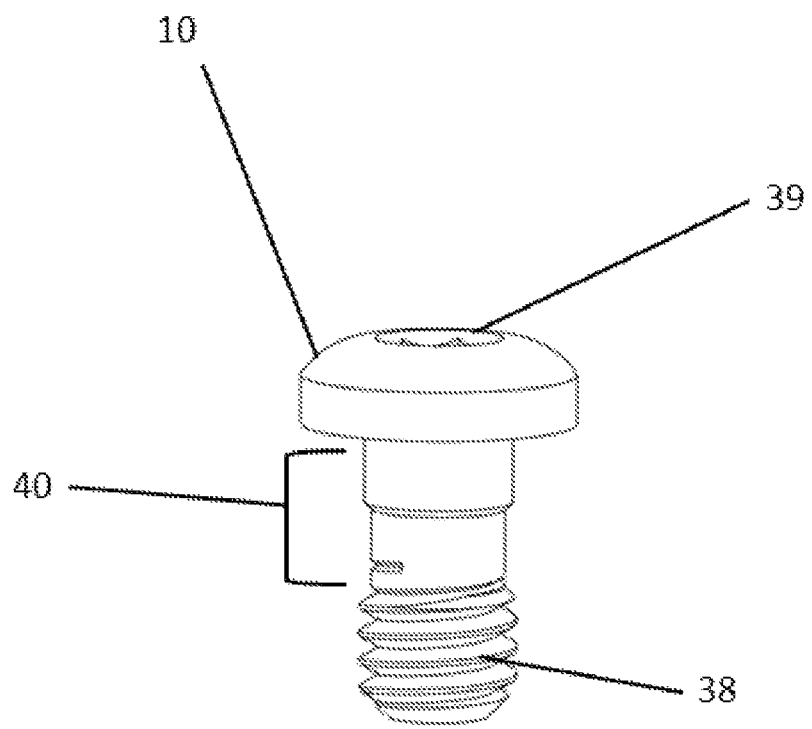
FIG. 8 is a perspective view of a poly lock screw, in accordance with embodiments.

The poly lock screw 10 may be coupled and/or locked onto the tibial tray 2 in various ways. For example, in a preferred embodiment, the poly lock screw 10 may comprise threads on a proximal end thereof (as shown in FIG. 8) which correspond to threads of the threaded aperture 37 of the tibial tray 2 (as shown in FIGS. 7b and 11). Alternatively, or in combination, a latch or a tapered press-fit may be provided which may allow for the same insertion method described herein with respect to the poly lock screw 10.

FIG. 8 shows a perspective view of a poly lock screw 10. The poly lock screw 10 may comprise threads on its proximal end 38 that are compatible to the ones found in the threaded apertures 16, 17 of the insert 3 and the tibial tray 2 as described herein. The head 39 of the poly lock screw 10 may comprise one or more features compatible to a driver such as a hex or torx. In a preferred embodiment, the head 39 may be fitted for a hex driver.

In some embodiments, the shaft 40 of the poly lock screw 10 may comprise two different diameters. In some embodiments, the shaft 40 of the poly lock screw 10 may comprise the same diameter. In some embodiments, the shaft 40 of the poly lock screw 10 may comprise more than two different diameters.

In some embodiments, the shaft 40 of the poly lock screw 10 may comprise a first diameter and a second diameter. A first diameter may be large enough for an interference fit with the threaded aperture 36 in the insert 3 and the second diameter may be small enough for a clearance fit through threaded aperture 36. The diameter dimensions of the shaft 40 may depend on the threads chosen for this connection and may be configured such that there is enough thread space for the shaft 40 to fit into the insert 3 and the tibial tray 2.

The poly lock screw 10 is made of an appropriate biocompatible material. For example, the poly lock screw 10 may be made of an appropriate biocompatible metal. For example, the poly lock screw 10 may comprise cobalt chromium, titanium, titanium-based alloys, stainless steel, or the like, or any combination thereof.

In some embodiments, the insert 3 may be configured such that it limits hyperextension of the system to a pre-determined amount. In some embodiments, as described herein, hyperextension may range from about 0 degrees to about 7 degrees. In a preferred embodiment, the system may be configured to allow for about 5 degrees of hyperextension.

Figure 9A:
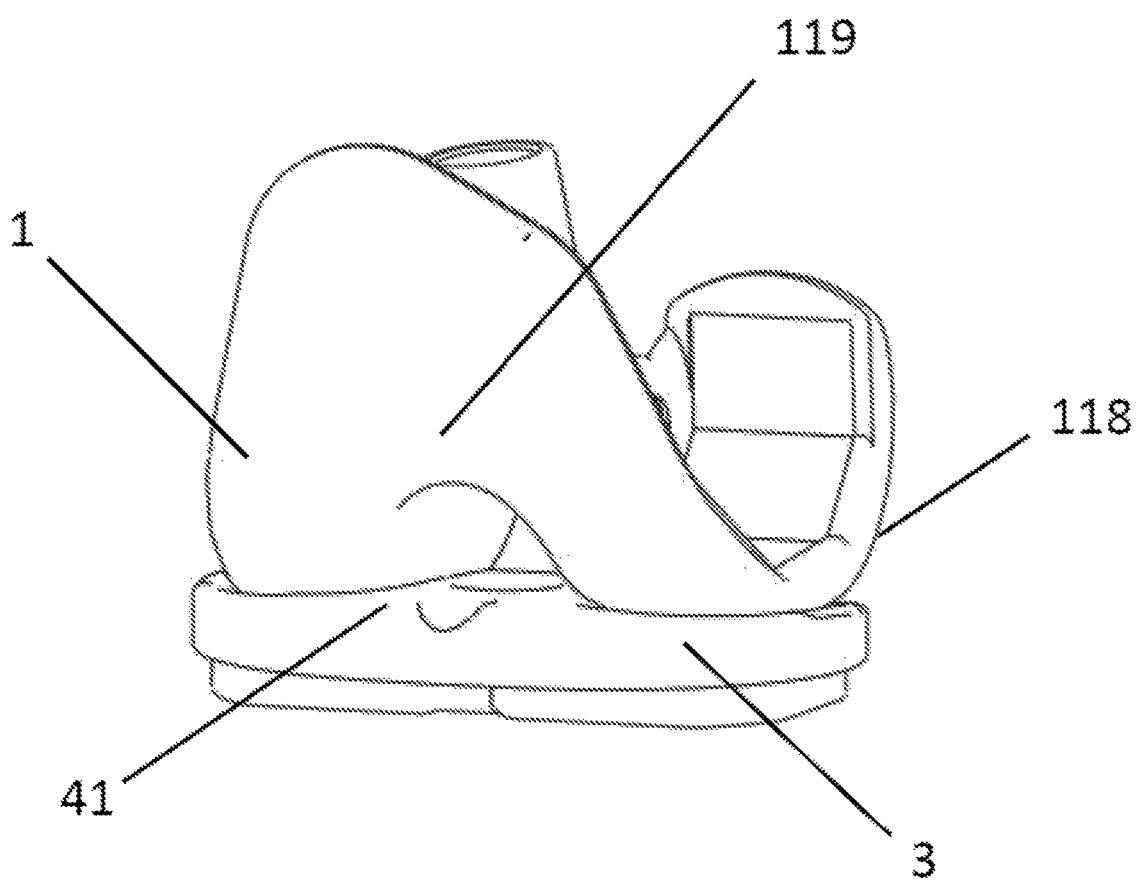
FIG. 9a is a perspective view of a femoral component sitting on an insert at hyperextension with a hyperextension block on an insert, in accordance with embodiments.
Figure 9B:
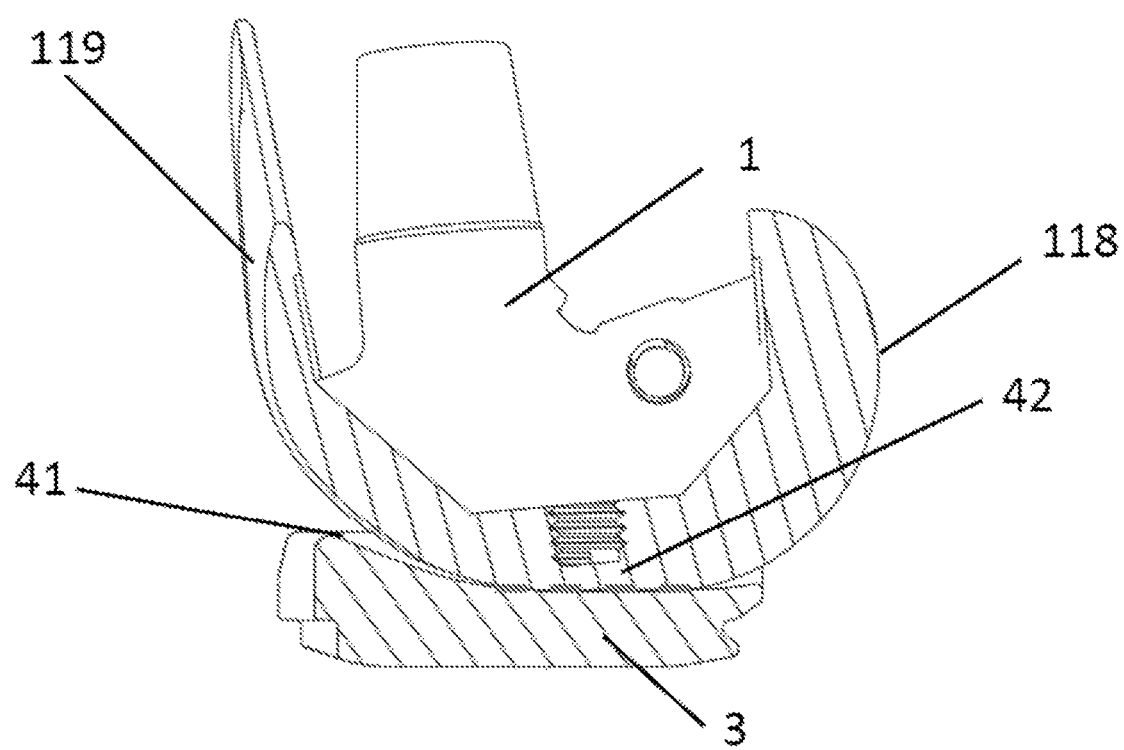
FIG. 9b is a lateral cross-sectional view of a femoral component stopped at hyperextension on an insert taken from the axis of a femoral condylar surface, in accordance with embodiments.

FIG. 9a shows a perspective view of a femoral component 1 sitting on an insert 3 at hyperextension with a hyperextension block 43 on an insert 3. FIG. 9b shows a lateral cross-sectional view of a femoral component 1 stopped at hyperextension on an insert 3 taken from the axis of a femoral condylar surface. In some embodiments, the insert 3 may be configured such that it limits hyperextension of the system. For example, the insert 3 may comprise one or more features configured to limit hyperextension. The one or more features may, for example, include an anterior buildup 41 of the insert 3. The anterior buildup 41 may be configured such that it not only stops the femur 1 from hyperextending (e.g., to the previously-described 5 degrees from the vertical plane), but it also limits the internal/external rotation when extended. The anterior buildup 41 may be configured for the position when the femoral component 1 is hyperextended such that it can only internally/externally rotate (e.g., to the 15 degrees previously described herein). The geometry of the anterior buildup 41 may be unique to each femoral component 1 size in the system as it may be configured to interact with the anterior face of the femoral component 1 and the intercondylar box 15, all of which may vary due to medial/lateral and anterior/posterior dimensions of the femoral component 1 as described herein. Once the femoral component 1 is flexed out of hyperextension, the anterior buildup 41 may no longer be in contact with the anterior portion of the femoral component 1 such that the rotation of the femoral component 1 may be dictated primarily by the condylar surface grooves 11 of the insert 3 as described herein, which may allow for more rotation (e.g., more than the 15 degrees previously described herein).

In some embodiments, the anterior buildup 41 may be part of a single-part construction insert 3. In some embodiments, the anterior buildup 41 may comprise a separate component from the insert 3 that can be fixed to the insert 3 onto the same location shown in FIG. 6a either before or after the insert 3 is implanted. The anterior buildup 41 component may be substantially similar in how it interacts with the anterior face of the femoral component 1 and the intercondylar box 15 to prevent hyperextension over the allowable amount defined in the system as described herein.

In some embodiments, a second (or alternative) feature may be provided. For example, a relatively flat portion 42 may be disposed along the condyle profile of the femoral component 1. The flat portion 42 may be configured such that the femoral component 1 bottoms out on the insert 3 when it reaches the desired angle of hyperextension. The degree of hyperextension allowed in the system may be similar to others in the art, which may range from about 0 degrees to about 7 degrees. The length of the flat portion 42 may vary for each femoral component 1 size provided in the system. The length of the flat portion 42 may be configured to fit between the features for the anterior trochlear groove 119 of the femoral component 1 and the posterior condyle profile 118. In a preferred embodiment, the system may allow for about 5 degrees of hyperextension. In this way, the flat 42 on the femoral component 1 may act as a hyperextension stop.

Figure 10:
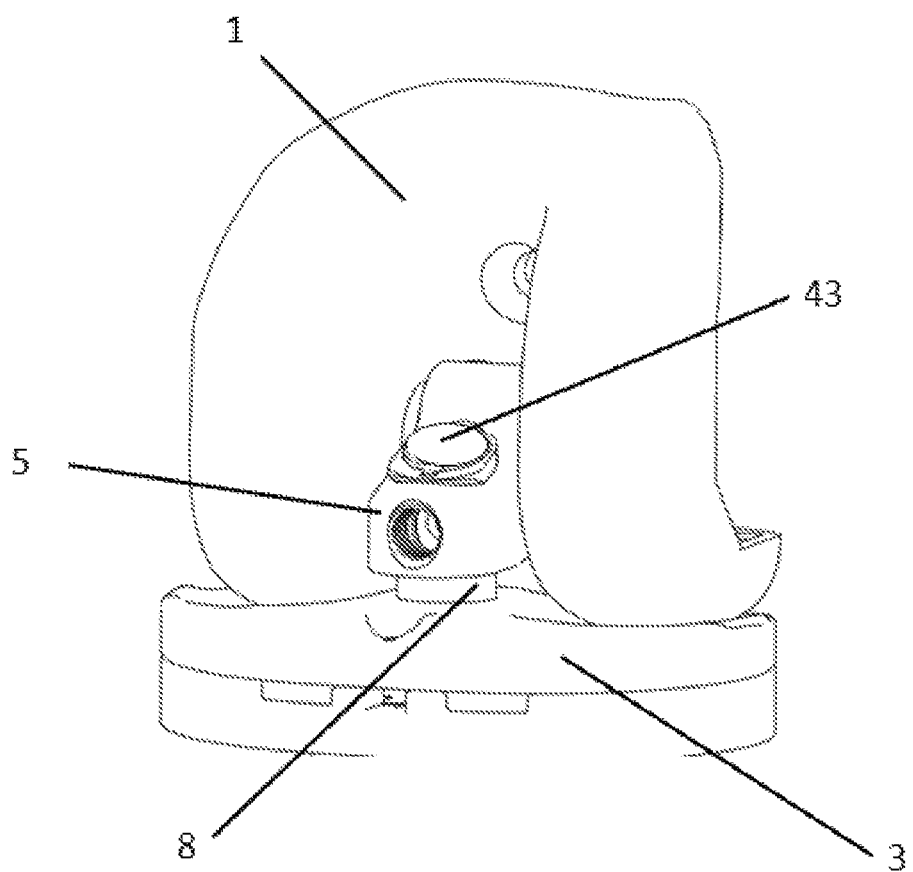
FIG. 10 is a perspective view of a hyperextension block embodiment with a femoral component in flexion and a hinge post assembled into a hinge box.

FIG. 10 shows a perspective view of a hyperextension block embodiment with a femoral component 1 in flexion and a hinge post assembly 8 assembled into a hinge box 5. Alternatively to, or in combination with, the embodiment shown in FIGS. 9a and 9b, a hyperextension block 43 may be coupled to the hinge box 5 and/or hinge post assembly 8 in order to limit hyperextension of the knee during use. The hyperextension block 43 may be disposed on the hinge post assembly 8 and may be configured to interact with the interior of the intercondylar box 15 of the femoral component 1 to prevent hyperextension.

In some embodiments, the hyperextension block 43 may be configured such that it limits hyperextension of the system to a pre-determined amount. The degree of hyperextension by the hyperextension block 43 may be within a range from about 0 degrees to about 7 degrees as described herein. In a preferred embodiment, the hyperextension block 43 may allow for about 5 degrees of hyperextension.

The hyperextension block 43 may comprise an appropriate biocompatible material. The hyperextension block 43 may comprise an appropriate biocompatible plastic. For example, the hyperextension block 43 may comprise a biocompatible polyethylene (e.g., UHMWPE), polyether ether ketone (PEEK), or the like, or any combination thereof.

Figure 11A:
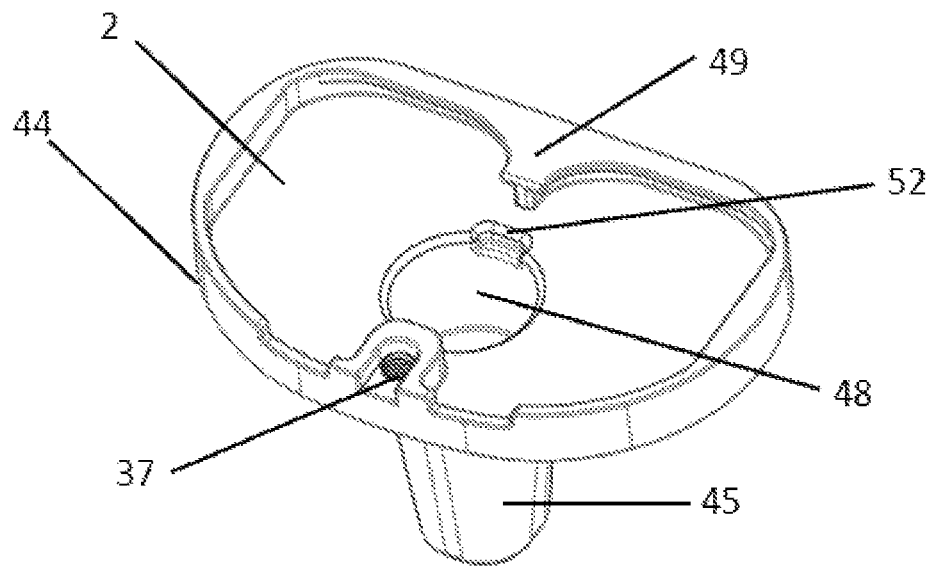
FIG. 11a is a perspective view illustrating proximal surface features of a tibial tray, in accordance with embodiments.
Figure 11B:
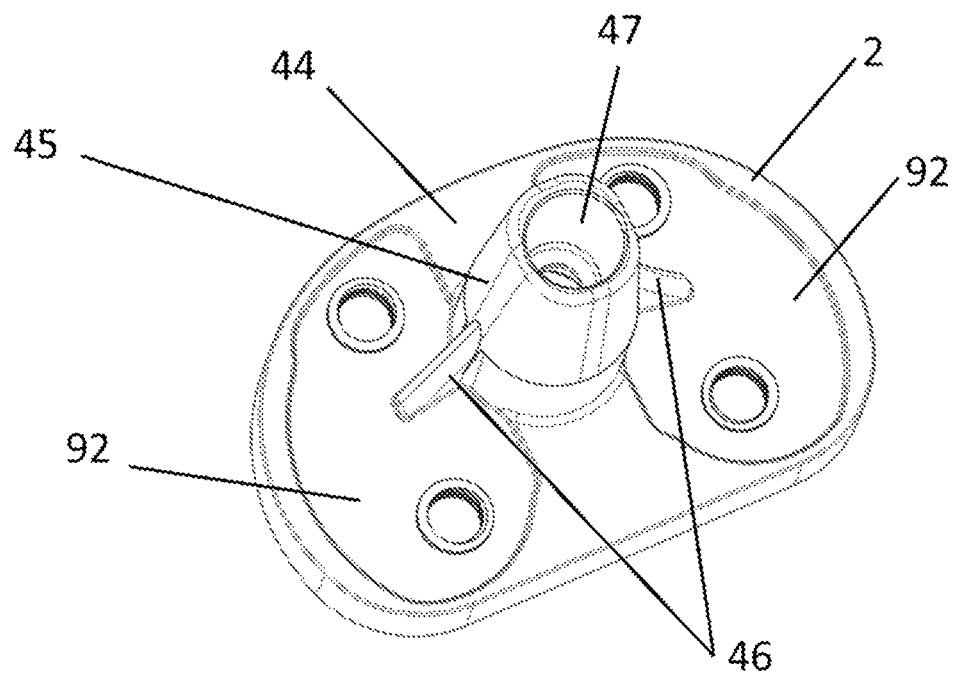
FIG. 11b is a perspective view of a distal surface of a tibial tray, in accordance with embodiments.

FIG. 11a shows a perspective view illustrating proximal surface features of a tibial tray 2. FIG. 11b shows a perspective view of a distal surface of the tibial tray 2. The tibial tray 2 may comprise a base 44 similar in shape to the insert 3 and a tibial post 45 with wings 46 as is common in the market. An aperture 47 (as shown in FIG. 11*b*) may be disposed on a distal end of the tibial post 45. The aperture 47 may be configured to be coupled to a stem extension (e.g., stem extension 112 shown in FIG. 13) should it be needed. The stem extension could be affixed to the tray 2 with a taper, a screw, of the combination, or any other connection mechanism described herein or understood by one of ordinary skill in the art based on the teachings herein. A tibial bushing aperture 48 may be disposed on the proximal surface of the base 44 of the tibial tray 2. Tibial bushing aperture 48 may be sized and shaped to correspond to a tibial bushing (e.g., tibial bushing 4 shown in FIGS. 12*a* and 12*b*) as described herein. One or more features on the proximal surface of the tibial tray 2 may be configured to interact with one or more features on the insert 3 to connect the two components as described herein. For example, the tibial tray 2 may comprise one or more posterior features 49 on the proximal surface of the base 44 of the tray 2 configured to interact with features (e.g., posterior portion 34 shown in FIG. 6*b*) on the insert 3 to connect the tray 2 to the insert 3. A feature on the proximal, anterior end may comprise a threaded aperture 37 configured to engage with the poly locking screw 10 (or another locking mechanism) as described herein. The distal surface of the tibial tray 2 may comprise one or more cement pockets 92 configured to contact the tibia and enable coupling of tibial tray 2 thereto.

In some embodiments, the tibial tray 2 may comprise a one-piece construction. In some embodiments, the tibial tray 2 may comprise a multi-piece construction.

The tibial tray 2 may comprise an appropriate biocompatible material. The tibial tray 2 may comprise an appropriate biocompatible metal. For example, the tibial tray 2 may comprise cobalt chromium, titanium, titanium-based alloys, stainless steel, or the like, or any combination thereof.

The tibial tray 2 may come in various sizes in the system. There may be as many sizes of tibial tray 2 as there are sizes of femoral component 1. The tibial tray 2 may be sized to be compatible with the femoral component 1 sizing. Compatibility in the system is defined as the femoral component 1 fitting and working with the correct range of motion described for each tibial tray 2 it can be implanted with. The tibial tray 2 sizes may be configured to fit a wide range of patient anatomy. The sizing, similar to the sizing of the femoral component 1, may be configured to fit a patient's previously-existing anatomy. In a preferred embodiment, the system may be configured with at least one femoral component 1 size which corresponds to at least one tibial tray 2 size (e.g., size 1 femoral component 1 corresponds to size 1 tibial tray 2, size 2 femoral component 1 corresponds to size 2 tibial tray 2, etc.) and optionally one size above and/or below (e.g., size 3 femoral component 1 corresponds to size 4 and/or size 2 tibial trays 2).

The tibial tray 2 dimensions may vary depending on the size of the components of the system. The tibial tray 2 dimensions may include the medial/lateral and anterior/posterior dimensions of the tibial base 44, the length and diameter of the tibial post 45, and the width and length of the wings 46.

Figure 12A:
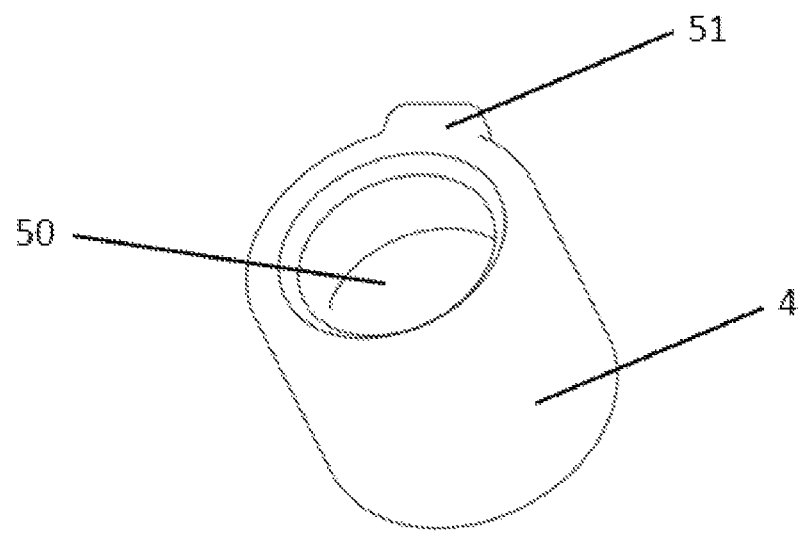
FIG. 12a is a perspective view of a tibial bushing, in accordance with embodiments.
Figure 12B:
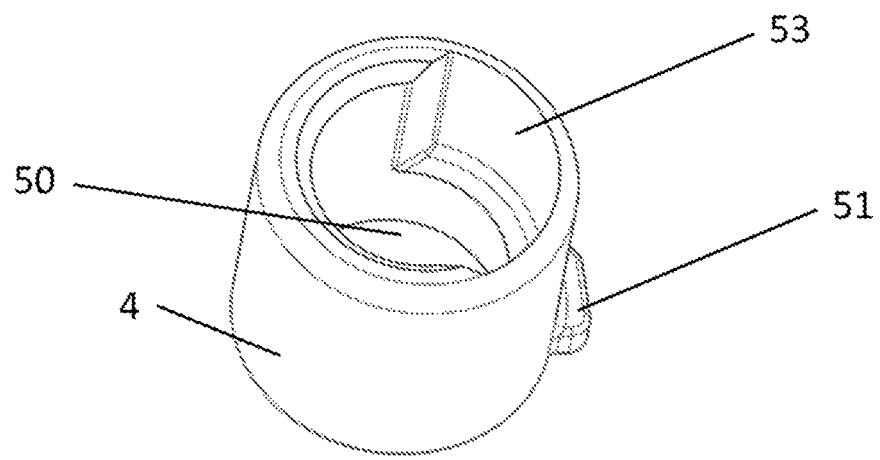
FIG. 12b is a perspective view of a hinge post assembly locking feature on the distal end of a tibial bushing, in accordance with embodiments.

FIG. 12*a* show a perspective view of a tibial bushing 4. FIG. 12*b* shows a perspective view of a hinge post assembly locking feature on the distal end of a tibial bushing 4. The tibial bushing 4 may comprise an aperture 50 through its center for the hinge post assembly 8. The tibial bushing 4 may be the same or different length as the aperture 48 in the tibial tray 2. In a preferred embodiment, the tibial bushing 4 may be press fit into the aperture 48 to secure it to the tibial tray 2. The tibial bushing 4 and tibial tray 2 may be pre-assembled together prior to surgery (e.g., during manufacturing or pre-operatively in the surgical suite). One or more features may be disposed on either or both of the tibial tray 2 and the tibial bushing 4 in order to ensure that the tibial bushing 4 is correctly oriented in the tibial tray 2. In a preferred embodiment, the bushing 4 may have a lip 51 on a posterior proximal end thereof. The lip 51 may be configured to fit into a matching pocket (e.g., pocket 52 shown in FIG. 11*a*) on the tibial tray 2. For the specific embodiment of the hinge post assembly described in herein (e.g., FIGS. 14-19*c*), the tibial bushing 4 may also include one or more cut out 53 on the internal, posterior distal end thereof. The cut out 53 may engage with and act as a secondary rotational stop for the hinge post tab 56 as shown in FIG. 13. Although internal-external rotation of the system may be constrained by the surface 11 of the insert 3 as described herein, the cut-out 53 may act as a secondary internal-external stop if needed (e.g., if the surface 11 fails or the rotational motion/toque applied to the knee exceeds the limits of the surface 11 on its own). The material above the cut-out 53, shown in the cross-sectional view of FIG. 13, may also acts as an axial stop for the hinge post tab 56 in order to keep the femoral component assembly from dislocating from the tibial components when the system is fully assembled.

An outside diameter of the tibial bushing 4 may be configured to be press-fit into the aperture 48 of the tibial tray 2. The tibial bushing 4 may be long enough to fully cover the hinge post assembly 8 when assembled in place as shown in FIG. 13. The length may be the same length as or a different length from the aperture 48 in the tibial tray 2. The diameter of the aperture 50 may be configured to allow for a clearance fit with the hinge post assembly 8.

The tibial bushing 4 may comprise an appropriate biocompatible material. The tibial bushing 4 may comprise an appropriate biocompatible plastic. For example, the tibial bushing 4 may comprise UHMWPE or a similar polyethylene.

FIG. 13 shows a lateral cross-section of the assembled hinge knee system of FIG. 1 without the DFR components added thereto. If needed, a stem extension 112 may be assembled onto the tibial tray aperture 47 prior to implantation (e.g., pre-operatively in the surgical suite) with connection techniques described herein. Once the tray 2, with the assembled tibial bushing 4 and optional stem extensions 112, is implanted into the tibia of the patient, the insert 3 may be placed onto the tibial tray 2 with connection techniques described herein. The hinge post aperture 32 of the insert 3 should be aligned to the aperture 50 of the tibial bushing 4. Properly aligning the hinge post aperture 32 with the aperture 50 may be important for ensuring the hinge post assembly 8 can be assembled. A stem extension 112 may optionally be assembled onto the stem connection 27 of the femoral component 1 before it is implanted with connection techniques described herein. The implanted femoral component 1 may then be moved into flexion such that the proximal end of the hinge box 5 is exposed to the user and the aperture 24 of the hinge box 5 is aligned closely to the aperture 32 of the insert 3. The hinge post assembly 8 may then be placed into the aperture 24 of the hinge box 5, through the aperture 32 of the insert 3, and into the tibial bushing 4 aperture 50 that sits within the tibial tray 2. The hinge post assembly 8 may then be engaged such that it locks the femoral components to the tibial components as described herein. In a preferred embodiment, the femoral and tibial components may be locked together via the hinge post tab's 56 interaction with the cut-out 53 of the tibial bushing 4. The final position of the hinge post assembly 8 may be such that the apertures 60, 70 are aligned with the aperture 26 of the hinge box 5. The hinge post assembly 8 may then secured in place to the hinge box 5 with a hinge set screw 9 that is assembled anteriorly into aperture 26 as described herein.

Figure 14:
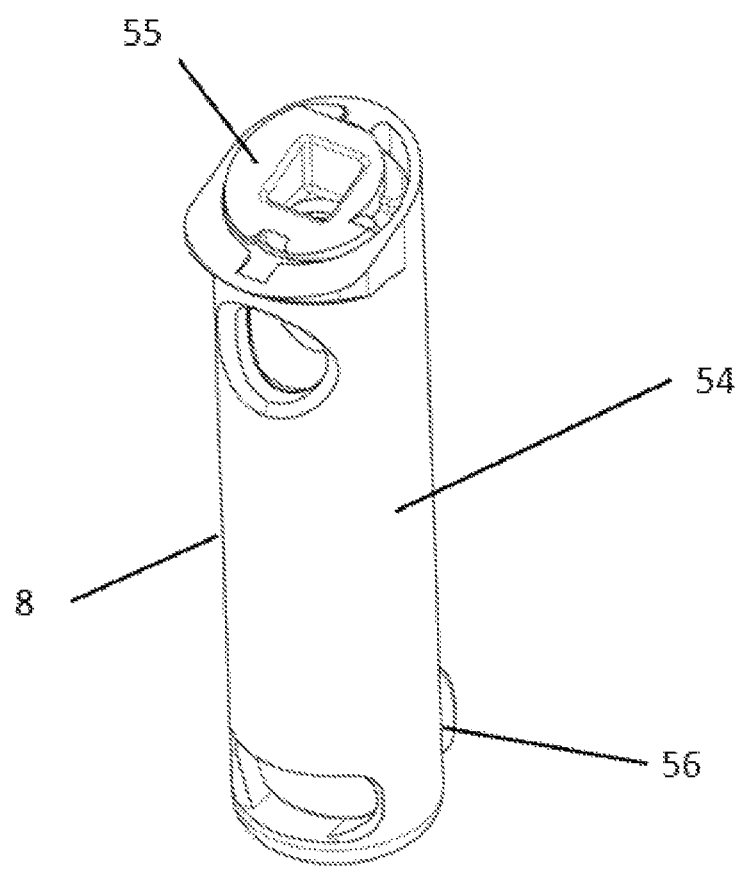
FIG. 14 is a perspective view of an assembled hinge post assembly in the locked position, in accordance with embodiments.
Figure 15:
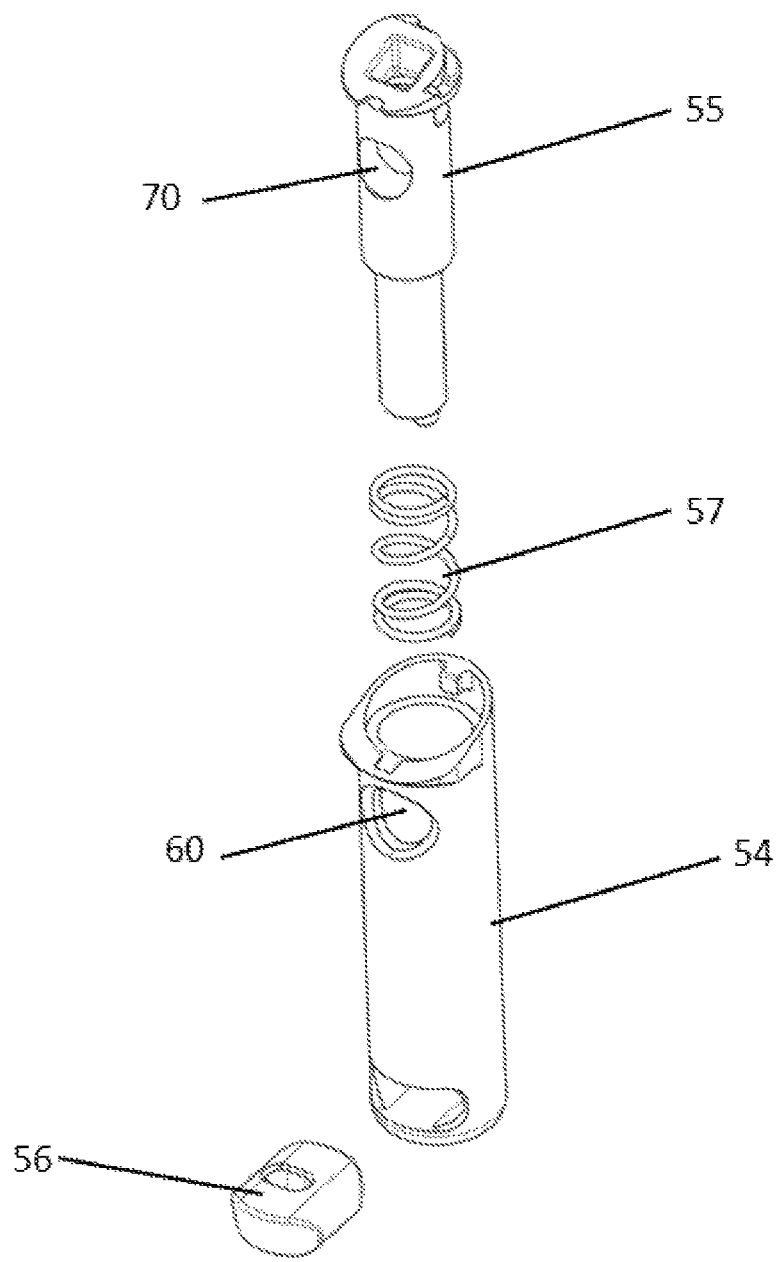
FIG. 15 is a perspective, exploded view of a preferred embodiment of a hinge post assembly, in accordance with embodiments.

FIGS. 14 and 15 show a preferred embodiment of the hinge post assembly 8. FIG. 14 shows the assembled hinge post assembly 8 assembled while FIG. 15 shows an exploded view of of the hinge pose assembly 8. The hinge post assembly 8 may be configured to connect the components attached to the femur and the components attached to the tibia together. The system described is a fixed hinge post design, which means it locks the femoral components to the tibial components such that the two have a predetermined amount of allowed axial dislocation, but cannot be completely separated from each other once the hinge post connects them. In a preferred embodiment, the system may allow for a minimum of about 1.5 mm of proximal distraction.

The hinge post assembly 8 may comprise a hinge post body 54, a hinge post shaft 55, a hinge post tab 56, and a spring 57.

The hinge post assembly 8 may comprise a biocompatible metal. For example, the hinge post assembly 8 components may comprise cobalt chromium, titanium, titanium-based alloys, stainless steel, or the like, or any combination thereof.

The hinge post body 54 may comprise a biocompatible metal. For example, the hinge post body 54 may comprise cobalt chromium, titanium, titanium-based alloys, stainless steel, or the like, or any combination thereof.

The hinge post shaft 55 may comprise a biocompatible metal. For example, the hinge post shaft 55 may comprise cobalt chromium, titanium, titanium-based alloys, stainless steel, or the like, or any combination thereof.

The hinge post tab 56 may comprise a biocompatible metal. For example, the hinge post tab 56 may comprise cobalt chromium, titanium, titanium-based alloys, stainless steel, or the like, or any combination thereof.

The spring 57 may comprise a biocompatible metal. For example, the spring 57 may comprise cobalt chromium, titanium, titanium-based alloys, stainless steel, or the like, or any combination thereof.

Figure 16:
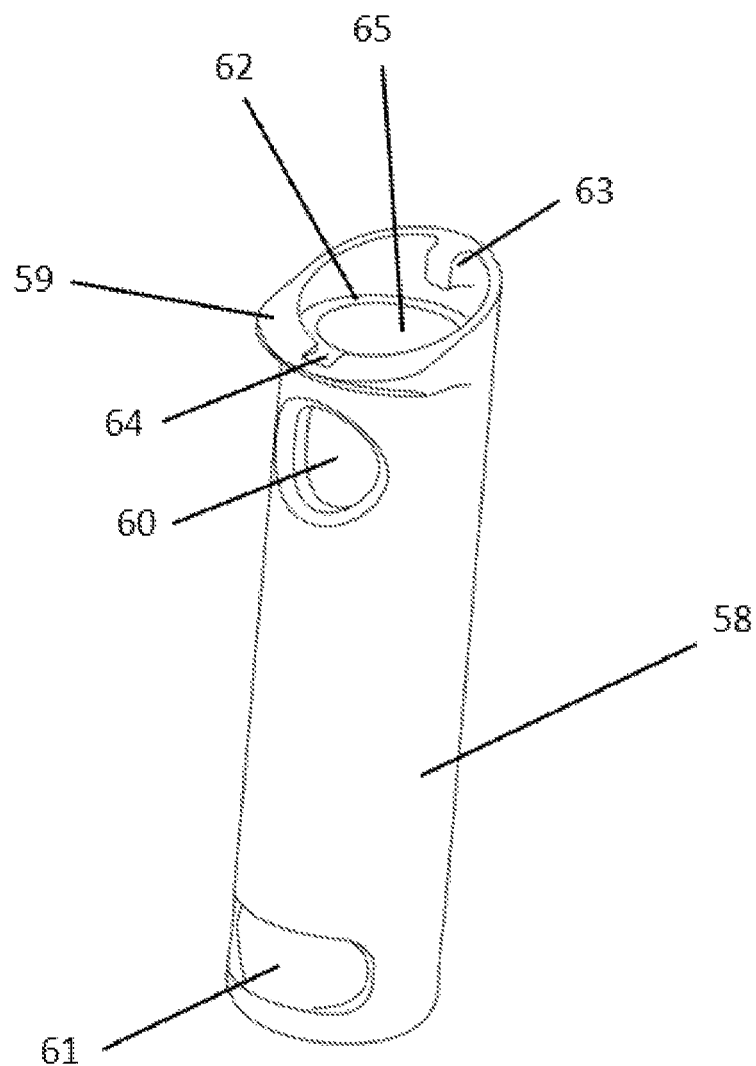
FIG. 16 is a perspective view of a hinge post body, in accordance with embodiments.

FIG. 16 is a perspective view of a hinge post body 54. The hinge post body 54 may have a uniform distal diameter shaft 58 and a proximal head 59 that has an overhang, tab, or pin only in the anterior direction. Due to loading conditions, the diameter of the hinge post body 54 may be at least about 9.5 mm. In a preferred embodiment, the diameter of the hinge post body 54 may be about 10 mm. The diameter of the hinge post shaft 58 may be smaller than the diameter of the hinge post body 54 so as to enable it to fit within the hinge post body 54 as described herein. The overhang on the head 59 may sit on the countersink 25 of the hinge box aperture 24 (shown in FIG. 4) to prevent the hinge post body 48 from falling through the hinge box 5. The overhang may be only be present on the anterior side of the hinge post body 54 in order to ensure enough wall thickness between the hinge post assembly 8 when assembled into the hinge box 8 and aperture 21 of the hinge box 5 for the bushings 6. The medial, lateral, and posterior sides of the hinge post body head 59 may follow the same shape and diameter as the hinge post body shaft 58, which in a preferred embodiments comprises a circular cross-sectional shape. The head 59 shape may be configured to both minimize the medial/lateral dimension of the hinge post such that it matches the diameter of the shaft 58 to ensure it fits into the aperture 24 of the hinge box 5 and the hinge box 5 still has a narrow enough width to fit between the intercondylar box 15 of the femoral component 1. The head 59 may also be configured to ensure the correct orientation of the hinge post assembly 8 into the hinge box 5 such that anterior aperture 60 on the hinge post body 54 is aligned with the threaded aperture 24 on the hinge box 5. In some embodiments, there may be another or an alternative orienting feature disposed on the hinge post body 54 configured to correctly orient the hinge post assembly 8 to the hinge box 5 such as a pin, a groove, a different overhang, a notch, or the like, or any combination thereof.

Figure 17A:
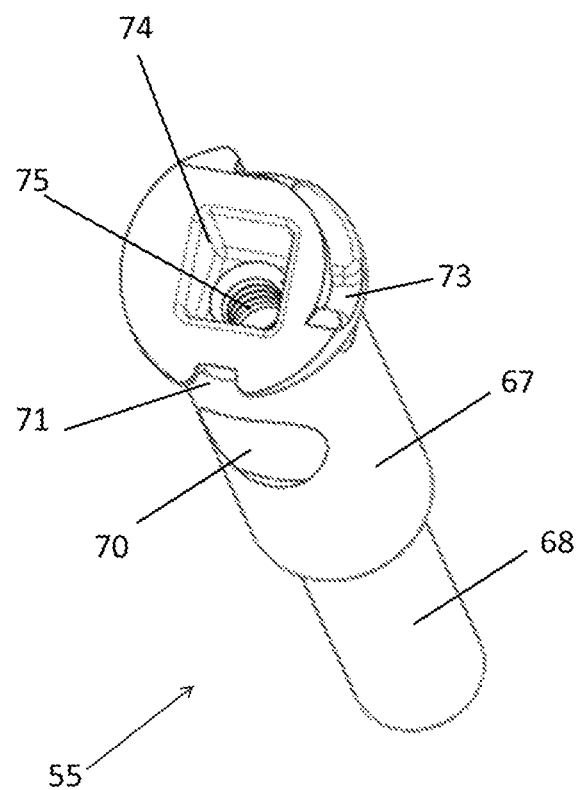
FIG. 17a shows a perspective view of a hinge post shaft, in accordance with embodiments.

An aperture 61 on the distal end of the hinge post body 54 may goes through the entire component. The aperture 61 may be large enough to hold the hinge post tab 56 for a clearance fit. The aperture 61 may be configured to hold the hinge post tab 56. There may also be a channel or lumen 65 that runs axially down the center of the hinge post body 54 from the head 59 to the distal aperture 61. The hinge post body 54 may be closed on the distal end. The hinge post body 54 may be open on the distal end as long as the hinge post tab 56 is held in place and can still function as described herein. The channel or lumen 65 may be configured to fit a hinge post shaft (e.g., hinge post shaft 55 shown in FIGS. 17a and 17b) fit therewithin. A lip 63 on the proximal-most side of the head 59 inside of the shaft channel 65 may guide and orient the insertion of the hinge post shaft 55. A small feature 64 (e.g., a slight notch as shown in FIG. 17a) configured to help the user orient the anterior direction of the component and to let the user know of the final rotational stop of the hinge post shaft 55 within the hinge post body 53 may be disposed on the anterior, proximal end of the head 59. The feature 64 may be a notch, a raised portion of material, a laser mark, or any other feature used in the art that helps orient a component. The head 59 may also comprise a countersink 62 configured to keep the hinge post shaft 55 in place such that it does not fall through into the hinge post body 54.

Figure 17B:
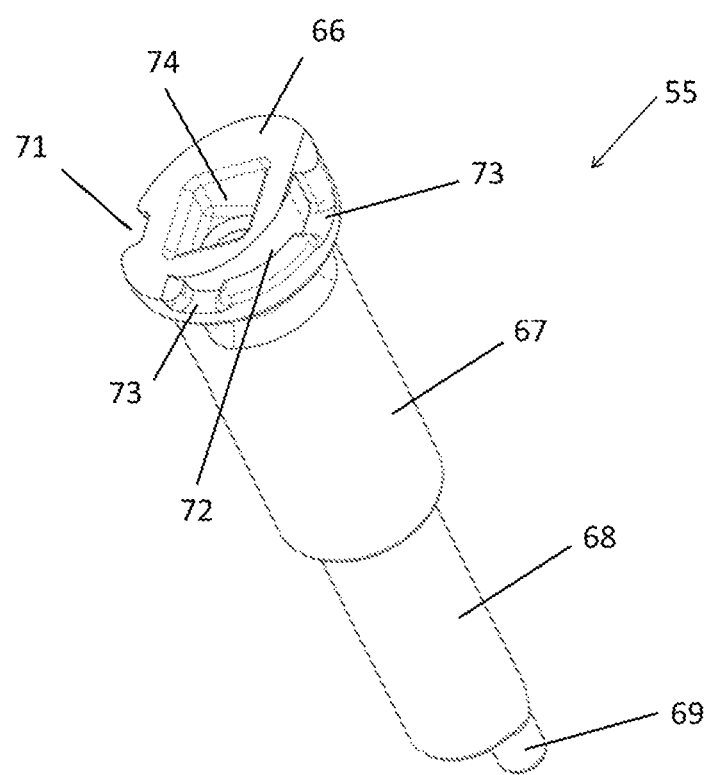
FIG. 17b shows a 90° rotated perspective view of the hinge post shaft of FIG. 17a, in accordance with embodiments.

FIG. 17a shows a perspective view of a hinge post shaft 55. FIG. 17b shows a 90° rotated perspective view of the hinge post shaft 55. The hinge post shaft 55 may comprise a uniform body configured to fit inside aperture 65 of the hinge post body 54. The hinge post shaft 55 may be rotatable within the hinge post body 54. The hinge post shaft 55 may comprise a proximal head 66, a uniform diameter shaft 67 below the head 66, a distal shaft 68 smaller in diameter below the shaft 67, and a distal feature 69 on the most distal end of the hinge post shaft 55. The diameter of the shaft 67 may have a clearance fit within aperture 65 of the hinge post body 54 so that it can rotate therewithin. The shaft 67 may comprise a uniform diameter along the length of the shaft 67 for strength purposes. It will be understood by one of ordinary skill in the art that the distal feature 69 can be of any cross-sectional shape, length, or width so as to be configured to engage a corresponding feature on the hinge post tab 56. It will be understood by one of ordinary skill in the art that the shape, length, and/or width of the distal feature 69 may be configured to fit within the hinge post tab 56 when fully assembled and may not greatly reduce the strength of the hinge post tab 56. The fit between the hinge post shaft 55 and the hinge post tab 56 may be a line to line or a clearance fit.

In a preferred embodiment, the distal feature 69 may comprise a small pin with a circular cross-section that is no longer than that hinge post tab 56. An aperture 70 may be disposed on the anterior side of the proximal shaft 67 to match the location of the aperture 60 on the hinge post body 54 when correctly rotationally aligned. The head 66 of the hinge post shaft 55 may follow the same profile as the head 59 of the hinge post body 54 when their anterior apertures 60, 70 are aligned. A notch cut 71 may be disposed on the anterior, proximal end of the head 66 and may be configured to match the lip feature 63 on the hinge post body 54. This cut 71 may not only guide the orientation the hinge post shaft 55 for assembly into the hinge post body 54, but also act as a visual guide to let the surgeons know when the hinge post shaft 55 is in its final, assembled position because it is then aligned to the anterior feature 64 on the hinge post body 54. The head 66 may be configured such that, after the hinge post shaft 55 is placed and rotated within the hinge post body 54, it cannot be pulled out because the lip 63 on the hinge post body 54 keeps it in place. A track 72 on the proximal head 66 may be configured to guide the allowed rotation of the hinge post shaft 55 within the hinge post body 54. The track 72 may be configured to allow for 90 degrees of rotation between the hinge post shaft 55 and the hinge post body 54 once they are assembled. One or more indents 73 may be disposed on the track 72 where the lip 63 of the hinge post body 54 fits in. In a preferred embodiment, these indents 73 may be located in pre-determined places that allow for quarter-turn rotations of the hinge post shaft 55 (e.g., as shown in FIGS. 19*b* and 19*c*). They may provide surgeons feedback on the correct location of the hinge post shaft 55 prior to, during, and after surgery. The proximal end of the hinge post shaft 55 may comprise an aperture 74 configured to engage with a hinge post instrument (e.g., hinge post instrument 76 shown in FIG. 20) for rotation. This aperture 74 can have various geometries such as a round or oval profile, but a preferred embodiment may comprise a square profile such that the instrument 76 can be engaged in any orientation without the need to align it to the hinge post assembly 8 to a specific orientation prior to use. The aperture 74 may also be configured to have a press-fit connection with the instrument 76. In some embodiments there may be an additional threaded aperture 75 inside the first that connects with the instrument 76 for reinforced engagement during insertion or removal of the hinge post assembly 8 from the hinge box 5 as described herein.

In some embodiments, the hinge post shaft 55 may comprise a unitary body. In some embodiments, the hinge post shaft 55 may comprise a multi-part construction.

Figure 18:
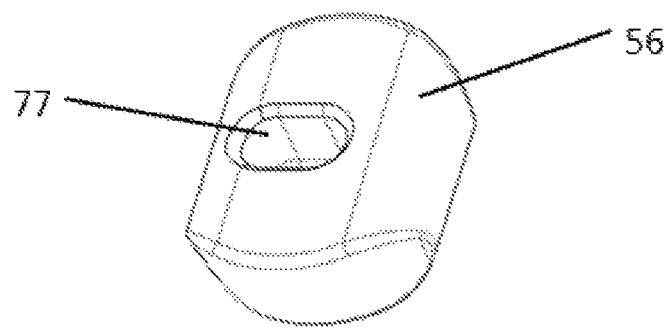
FIG. 18 is a perspective view of a hinge post tab, in accordance with embodiments.

FIG. 18 shows a perspective view of a hinge post tab 56. The hinge post tab 56 may be configured to fit into the aperture 61 on the distal end of the hinge post body 54. The hinge post tab 56 may be the same length as the diameter of the hinge post body shaft 58 such that it does not stick out when fit through the aperture 61. Keeping the hinge post tab 56 from sticking out of the hinge post body shaft 58 may ensure that the hinge post assembly 8 can be fit through all of the necessary apertures described herein. The hinge post tab 56 may comprise an aperture 77 on the proximal surface configured to engage with the distal feature 69 (shown in FIG. 19*a*) of the hinge post shaft 55. This aperture 77 may be placed in a location such that its interaction with the hinge post shaft 55, when rotated, translates the hinge post tab 56 within the aperture 69 of the hinge post body 54.

In some embodiments, the hinge post tab 56 may comprise a unitary body. In some embodiments, the hinge post tab 56 may comprise a multi-part construction.

Figure 19A:
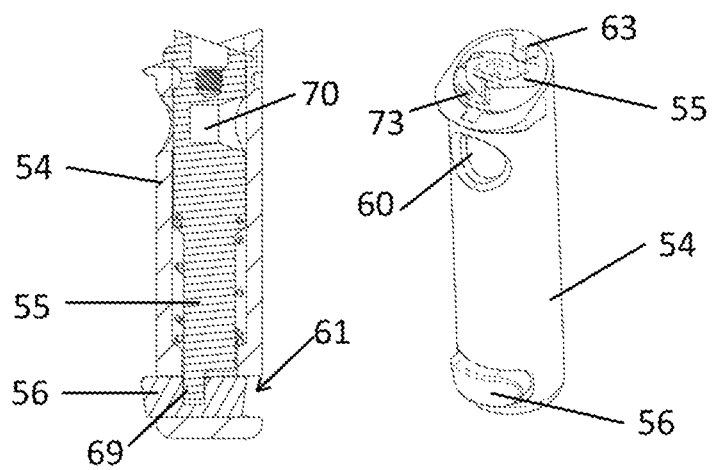
FIG. 19a shows a lateral cross-sectional view (left) and a perspective view (right) of an assembled hinge post assembly in a manufactured configuration, before any rotation of the hinge post shaft, in accordance with embodiments.
Figure 19B:
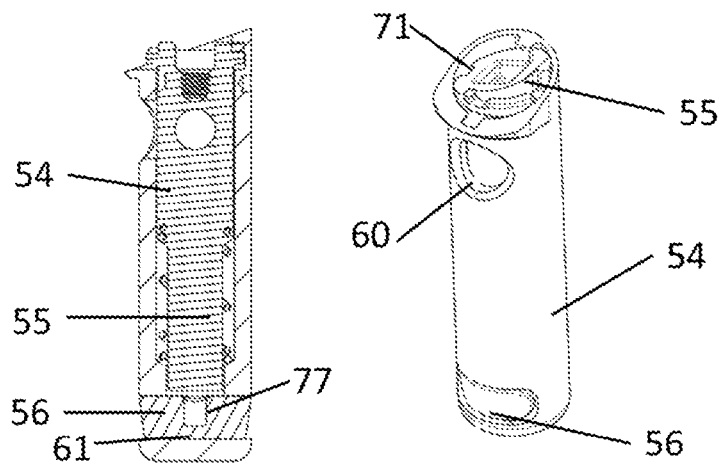
FIG. 19b shows a lateral cross-sectional view (left) and a perspective view (right) of the assembled hinge post assembly of FIG. 19a after the hinge post shaft has been rotated 90 degrees into a packaged configuration which is ready for use in surgery, in accordance with embodiments.
Figure 19C:
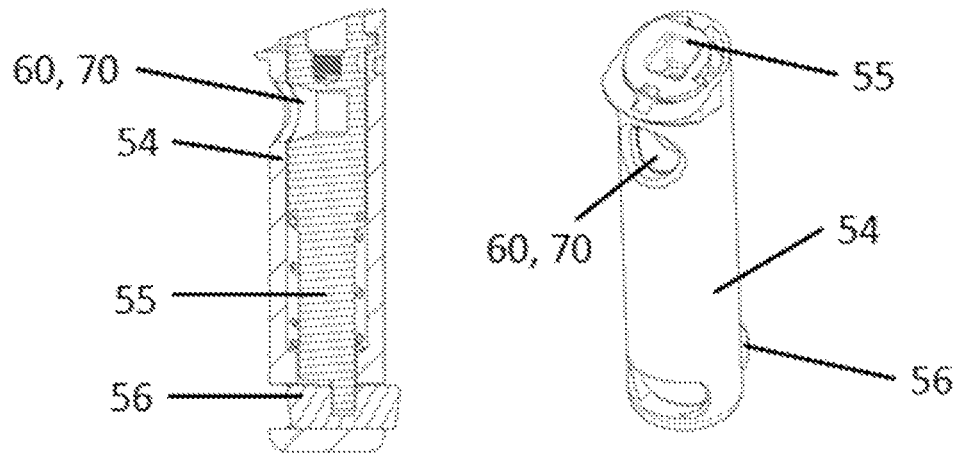
FIG. 19c shows a lateral cross-sectional view (left) and a perspective view (right) of the assembled hinge post assembly of FIG. 19b after the surgeons rotate the hinge post shaft 90 degrees to engage the hinge post tab into the locked configuration in the assembly, in accordance with embodiments.

FIG. 19*a* shows a lateral cross-sectional view (left) and a perspective view (right) of an assembled hinge post assembly 8 in a manufactured configuration. The hinge post assembly 8 may be pre-assembled during manufacturing. The hinge post tab 56 may be inserted into the distal aperture 61 of the hinge post body 54 such that it extrudes anterior slightly as seen in FIG. 19*a*. A medical grade spring 57 may then be then placed distally onto the hinge post shaft 55 to fit over the distal shaft 68 of the hinge post shaft 55. The hinge post shaft 55 and spring 57 may then be inserted into the hinge post body 54 such that the notch cut 71 on the hinge post shaft 55 fits over the lip 63 of the hinge post body 54 and the distal feature 68 of the hinge post shaft 55 is inserted into the aperture 77 of the hinge post tab 56. The square distal feature 88 of the hinge post instrument 76 may then be engaged onto the square aperture 74 of the hinge post shaft 55 and the hinge post shaft 55 is turned 90 degrees to the configuration shown in FIG. 19*b*.

FIG. 19*b* shows a lateral cross-sectional view (left) and a perspective view (right) of the assembled hinge post assembly 8 after the hinge post shaft 55 has been rotated 90 degrees within the hinge post body 54 into a packaged configuration which is ready for use in surgery. In the packaged configuration, the lip 63 on the hinge post body 54 may sit in one of the indents 73 of the hinge post shaft 55 and the force of the spring 57 may keep it engaged until the hinge post shaft 55 is pressed and rotated again. In some embodiments, another biasing feature such as a level may replace or be added to the spring 57 to keep the lip 63 engaged. The hinge post tab 56 may sit completely inside the hinge post body 54. At this point, the assembly 8 may be fixed such that the assembly 8 cannot turn back and disassemble. This could be done in various ways, including a pin, a swage, or any other methods in the art. The hinge post assembly 8 in the packaged configuration may be how the assembly is packaged and given to the surgeons. In this orientation, the hinge post assembly 8 is ready for insertion and use in the surgery.

Figure 20:
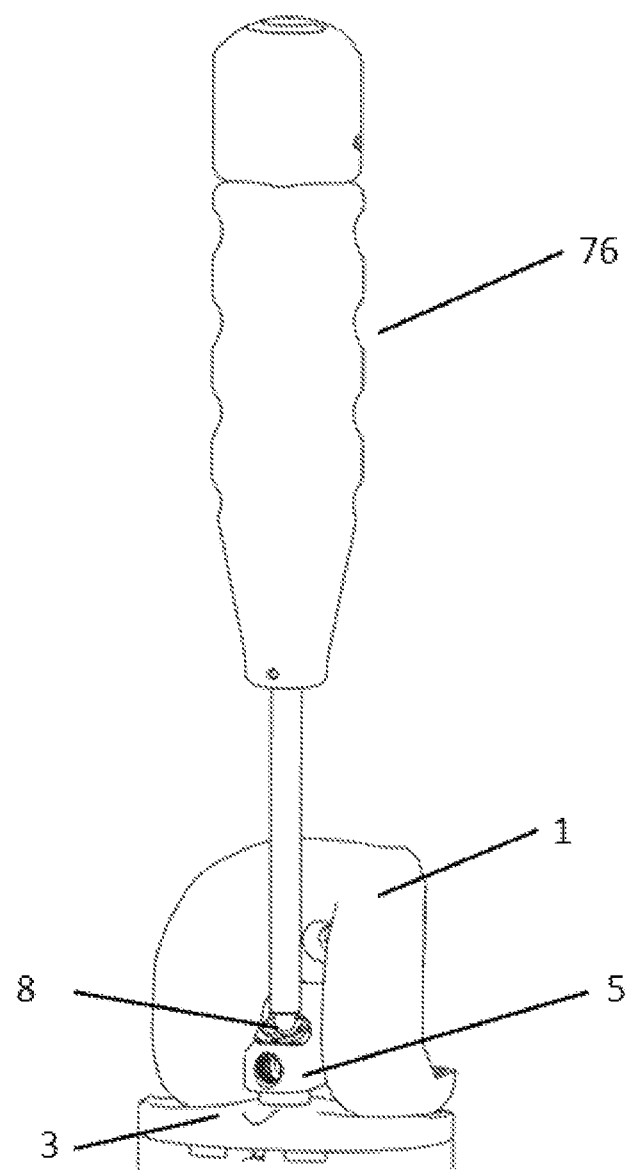
FIG. 20 shows a hinge post instrument configured for accessing the hinge post assembly (during insertion and/or removal) coupled to a femoral component, with the femoral component in flexion, in accordance with embodiments.

FIG. 19*c* shows a lateral cross-sectional view (left) and a perspective view (right) of the assembled hinge post assembly 8 after the surgeons rotate the hinge post shaft 55 an additional 90 degrees to engage the hinge post tab 56 into the locked configuration in the assembly 8. During surgery, when the surgeon is ready to fix the femoral components to the tibial components, they may flex the femur in order to provide themselves access to the hinge box 8 and enable insertion of the hinge post assembly 8 into the aperture 24 of the hinge box 5, through the insert 3, and into the tibial bushing 4. The hinge post instrument 76 may then be engaged into the hinge post assembly 8 as shown in FIG. 20, pushed down into the hinge post body 54, and rotated 90 degrees into the next indent 73 on the hinge post shaft 55. This rotational motion may cause the hinge post tab 56 to translate such that it extrudes posteriorly out of the hinge post body 54 as shown in FIG. 19*c*. In this position, as shown in the cross-sectional view of the entire system in FIG. 13, the hinge post tab 56 may fit inside the cut-out 53 of the tibial bushing 4. The engagement between the hinge post tab 56 and the tibial bushing 4 may lock the femoral components to the tibial components. The hinge post assembly 8 may then be fixed to the hinge box 5 as described herein.

The hinge post assembly 8 may be configured with the same diameter regardless of the size of the remaining components. For example, the hinge post assembly 8 may comprise a diameter of at least about 9.5 mm. The hinge post assembly 8 may be configured with different lengths that correspond to the different thicknesses of the insert 3 sizes provided in the system as described herein. For ease of use, the hinge post assembly 8 may be labeled with lasermarks and/or on the label of the packaging to match with the corresponding insert 3 and the hinge post assembly may be packaged with the hinge post set screw 9.

FIG. 20 shows a hinge post instrument 76 configured for accessing the hinge post assembly 8 (during insertion and/or removal as described herein) coupled to a femoral component 1, with the femoral component 1 in flexion. The hinge post instrument 76 may be configured to rotate at least a portion of the hinge post assembly 8, for example hinge post shaft 55 and/or hinge post tab 56 within hinge post body 54, in order to lock or unlock various components thereof to or from the femoral component 1, insert 3, and/or hinge box 5 as described herein.

Figure 21:
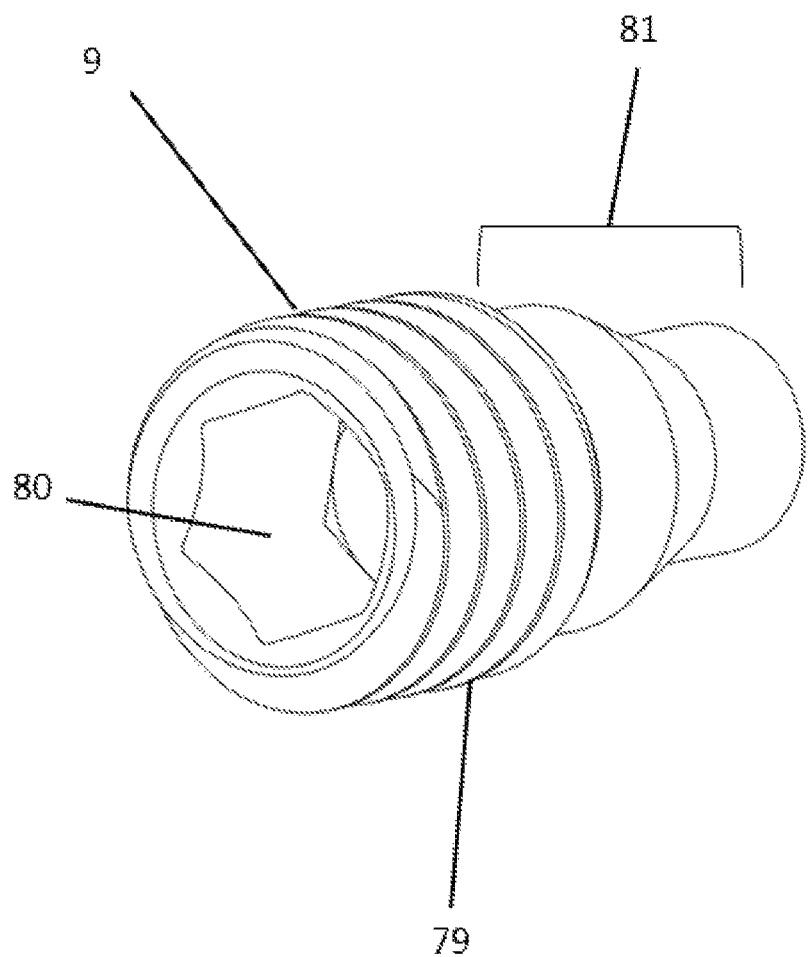
FIG. 21 is a perspective view of a hinge post set screw, in accordance with embodiments.

FIG. 21 shows a perspective view of a hinge post set screw 9. The use of a screw to fix the hinge post assembly 8 to the hinge box 5 is only one possible embodiment described herein of how fixation could be achieved. In a preferred embodiment, the hinge post set screw 9 may comprise threads 79 on its proximal end that are compatible to the ones found in the anterior aperture 26 of the hinge box 5. The head 80 of the hinge post set screw 9 may comprise one or more features compatible to a driver such as a hex, torx, or a similar driver. In a preferred embodiment, the head 80 may be configured for a hex driver. With the hinge post assembly 8 correctly placed in the hinge box 5 such that the apertures 60, 70 in the hinge post assembly 8 are aligned with the anterior aperture 26 of the hinge box 5, the hinge post set screw 9 may be threaded through the threaded aperture 26 of the hinge box 5. In the assembly described herein and shown in FIG. 13, a distal end 81 of the hinge post set screw 9 may be engaged inside the anterior apertures 60, 70 of the hinge post assembly 8. Once the hinge post set screw 9 is threaded into place, the hinge knee assembly is complete.

The hinge post screw 9 may comprise a biocompatible metal. For example, this hinge post screw 9 may comprise cobalt chromium, titanium, titanium-based alloys, stainless steel, or the like, or any combination thereof.

Although a preferred embodiment of the attachment between the hinge post assembly 8 and the hinge box 5 has been described with reference to a screw 9, it will be understood by one of ordinary skill in the art that there may be alternate anterior assembly embodiments that may also be used to affix the two components. One such embodiment may require the hinge post assembly 8 to be placed in the hinge box 5 and a set screw, pin, or clip may then be inserted anteriorly into the hinge box 5 such that it sits above the proximal end of the hinge post assembly 8 and keeps it in place. In another embodiment, there could be a latch mechanism in the hinge box 5 that locks into a notch in the hinge post assembly 8. The latch may be pressed so the hinge post assembly 8 is placed into a countersink of the hinge box 5 and it keeps the hinge post 8 in place when released. Another embodiment could include a bal seal around the aperture 24 in the hinge box 5 configured to engage with a circumferential groove on the hinge post body 54. In another embodiment, the hinge post assembly 8 could be impacted into place so a tapered proximal end engages with a female taper on the aperture 24 of the hinge box 5. Those are only some example embodiments, as there are other possible ways the hinge post assembly 8 could be affixed to the hinge box 5 which may be understood by one of ordinary skill in the art based on the description herein.

Figure 22:
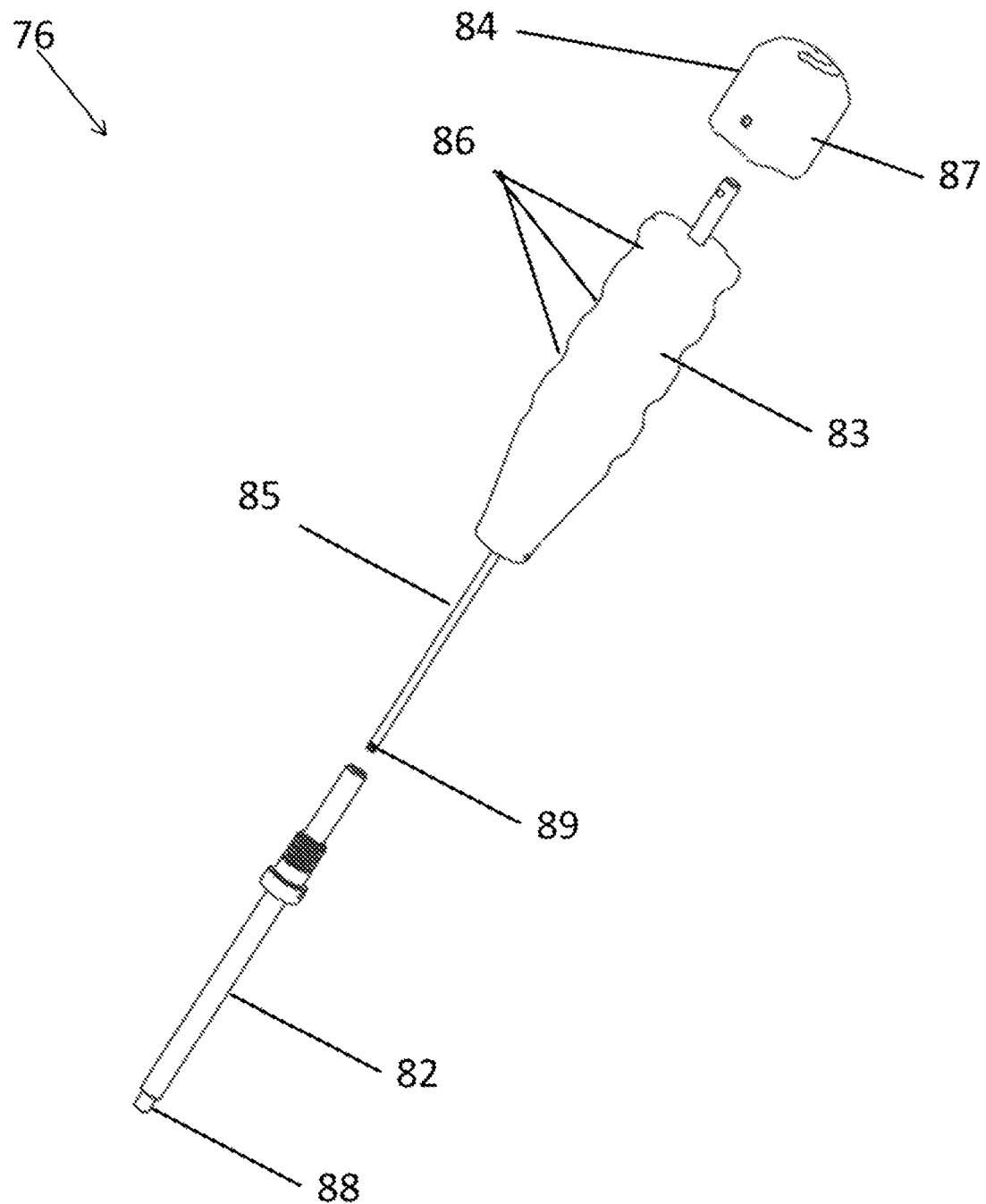
FIG. 22 is a perspective, exploded view of a hinge post instrument assembly, in accordance with embodiments.

FIG. 22 shows a perspective exploded view of a hinge post removal tool 76. The instrument 76 may comprise a shaft body 82 configured to engage the hinge post shaft 55 as described herein and an instrument handle 83. In a preferred embodiment, the instrument 76 may further comprise a turn-knob 84 located on the proximal end of the handle 83 and an internal shaft 85 which is connected to the turn-knob 84 and free to rotate within the hollow shaft body 82. The handle 83 may be made of an appropriate material such as radel or a similar plastic and may comprise grooves 86 along the circumference as shown. The grooves 86 are only an example embodiment of the groove geometry as they can vary in shape and may be configured for ergonomic preference of the user. The grooves 86 may run vertically, horizontally, or along both directions of the handle such that the handle is comfortable to grip for various hand sizes. The turn-knob 84 may be a uniform component made of a similar material as the handle 83. The turn-knob 84 may be configured to connect to and turn the internal shaft 85. The turn-knob 84 may comprise one or more grooves 87 that make it easier to grip and turn for the user. The knob 84 could also have one or more features on its proximal end such as a rounded head or a metal proximal head that allows for light tapping during insertion and removal of the hinge post assembly 8. The knob 84 may be configured to allow for rotation in either direction. In some embodiments, the knob 84 may be configured to prevent its removal from the internal shaft 85 by the user once it has been assembled after manufacturing.

The shaft body 82 may comprise a distal end 88 configured to correspond to the aperture 74 on the hinge post shaft 55. The shaft body 82 may be made of an appropriate material such as stainless steel or a similar metal. In a preferred embodiment, the distal end 88 may comprise a symmetric profile for ease of use, such as preferably a circle or more preferably a square a profile. The distal end 88 may comprise a profile which corresponds to the shape of aperture 74. The shaft body 82 may be hollow and the internal shaft 85 may be configured to fit within and rotate within the shaft body 82.

The internal shaft 85 may comprise a uniform component made of a metal similar to the shaft body 82 described herein. The proximal end of the internal shaft 85 may be configured to engage with and fit into the turn-knob 84 such that rotation of the turn-knob 84 relative to the handle 83 causes rotation of the internal shaft 85. The internal shaft 85 may be configured to fit within at least a portion the handle 83 and at least a portion of the hollow shaft body 82. The internal shaft 85 may comprising a length sufficient to engage with the turn-knob 84 and extend a few millimeters past the distal end 88 of the shaft body 82 when exposed. The internal shaft 85 may be configured to engage with features such as a spring and/or an internal feature on the handle 83, for example, to allow it to protrude past the distal end 88 of the shaft body 82 or sit within it such that it is not exposed. The instrument 76 may be configured so that when fully-assembled (e.g., when the internal shaft 85, connected to the turn-knob 84, is placed through the handle 83 and then the shaft body 82 is slide over the internal shaft 85 and connected to the handle 83), the distal end 88 of the internal shaft 85 does not come out past the shaft body 82. A spring, lever, latch, or the like may be used to keep the internal shaft 85 in place until the turn-knob 84 is pressed in towards the handle 83 and only then is the distal end 89 of the internal shaft 85 exposed.

The distal tip 89 of the internal shaft 85 may be threaded to engage and lock into the aperture 75 of the hinge post shaft 55. The distal tip 89 may be about the same length as the aperture 75. The distal end 88 of the shaft body 82 may be configured to install and lock the hinge post assembly 8 with just a press-fit between the two components whereas the distal tip 89 of the internal shaft 85 may be configured to remove or unlock the hinge post assembly 8 from the femoral and tibial components.

Should removal or replacement of the system be needed, the femoral component 1, tibial tray 2, and insert 3 can be removed with available instruments in a similar manner as a primary or revision system. The hinge components could also be replaced or removed if needed. If the hinge post assembly 8 needs to be replaced, the same instrument used to insert the hinge set screw 9 may be used to first remove the hinge set screw 9. In a preferred embodiment, the hinge post instrument 76 can then be used to remove the hinge post assembly 8 by first engaging (e.g., with a press-fit) the distal end 88 of the shaft body 82 to the aperture 74 hinge post shaft 55. The distal threads 89 on the inner shaft 85 should then be pushed out by pressing the turn-knob 84 and then threading them into the threaded aperture 75 of the hinge post shaft 55 using the knob 84. Once the hinge post instrument 76 is fixed onto the hinge post shaft 55, the hinge post assembly 8 can be disengaged from the tibial bushing 4 and pulled out. In the example embodiment of the hinge post assembly 8 described here, this may be done by having the surgeon turn the hinge post shaft 55 counter-clockwise. This action may translate the hinge post tab 56 anteriorly such that it now sits flush within the hinge post body 54, as seen in FIG. 19*b*. The hinge post assembly 8 can then be pulled out with the hinge post instrument 76. Should the cross-pin 7 need to be replaced, the surgeon could access the head of the cross-pin 7 laterally and use a hex provided in the instrument tray of the system to remove. If the bushings 6 need to be replaced, the hinge post assembly 8 should be removed first, followed by the cross-pin 7, before the hinge box 5 is be removed to access and replace the bushings 6.

Figure 23:
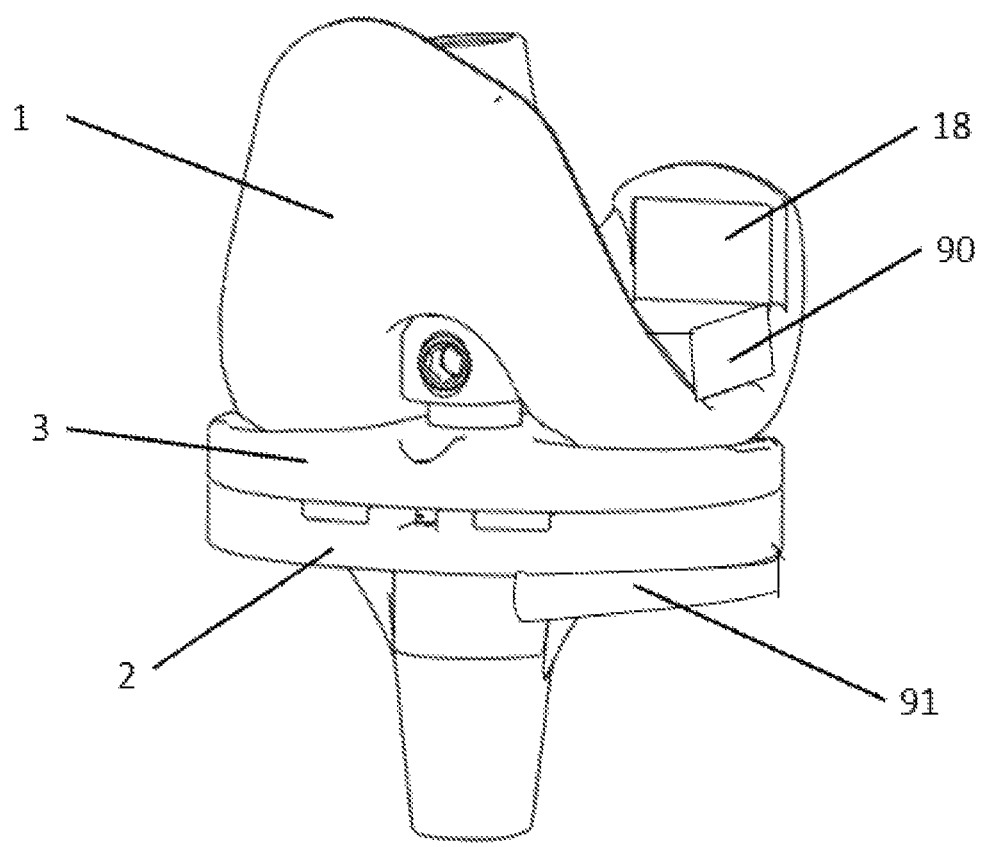
FIG. 23 is a perspective view of a hinge knee system assembled with femoral and tibial augments, in accordance with embodiments.

FIG. 23 shows a perspective view of the hinge knee system with optional femoral augments 90 and tibial augments 91. The augments 90, 91 may comprise an appropriate biocompatible metal such as cobalt chromium, titanium, titanium-based alloys, stainless steel, or the like, or any combination thereof. The augments 90, 91 may be packaged with the rest of the system should they be needed if there is any bone loss or resections that may be present during surgery. Left and right femoral augments 90 may be provided in the system. The left and right femoral augments 90 may be configured to fit on either end of the intercondylar box 15 and may be no wider than the condylar bearing surfaces 12 so as not to impinge on soft tissue outside the edges of the femoral component 1. The distal surface of the augments 90 may be configured to fit into the cuts 13 on the proximal surface of the condylar bearing surfaces 12 of the femoral component 1. The tibial augment 91 may be configured to match the shape of the symmetric tibial tray base 44. Because the base 44 is preferably symmetric and the tibial augments 91 are only about half the shape of the base 44, they can be used either on the left or right side of the tibial tray 2.

The femoral augments 90 may be provided in a number of different heights to accommodate varying bone loss in the patient. The femoral augments 90 may comprise a height greater than 5 mm. In some embodiments, the femoral augments 90 may comprise multiple different heights in increments. For example, the femoral augments 90 may be provided in heights of 5 mm and 10 mm.

The tibial augments 91 may be provided in a number of different heights to accommodate varying bone loss in the patient. The tibial augments 91 may comprise a height greater than 5 mm. In some embodiments, the tibial augments 91 may comprise multiple different heights in increments. For example, the tibial augments 91 may be provided in heights of 5 mm and 10 mm.

The augments 90, 91 can be attached to the femur or tibia, respectively, in a number of ways, such as with cement, screws, or a snap fit, or the like, or any combination thereof, as will be understood by one of ordinary skill in the art based on the teachings herein. In a preferred embodiment, augments may be affixed with either (or both) of (a) a bone cement similar to ones in the art, in which case the augments may comprise one or more cement pockets 92 on the edges that will be in contact with the femoral component 1, the tibial tray 2, or bone; or (b) one or more augment screws 92 of an appropriate length to engage into the threaded augment screw apertures on the tibial tray 2 and femoral component 1 as shown in FIGS. 2 and 11.

Additional femoral components may be included in the system to treat DFR cases. For DFR cases, additional resection is required of the distal femur that is not done in primary or revision surgery. An additional DFR cutting guide may be provided in the system to guide the additional resection on the femur. The DFR cutting guide may be used during a case where the distal femur has been previously resurfaced in a primary or revision knee surgery or in a case where the hinge knee DFR system will be the first surgery and the femoral condyles of the patient are still present. After the distal femur is resected to the appropriate length, the bone may be replaced with augments. Depending on the length of resected distal femur, the surgeon may decide to treat the case using the combination of a DFR augment (such as DFR augment 93 shown in FIGS. 24-25) and/or a DFR femoral component (such as DFR femoral component 94 shown in FIGS. 27-28.

Figure 24:
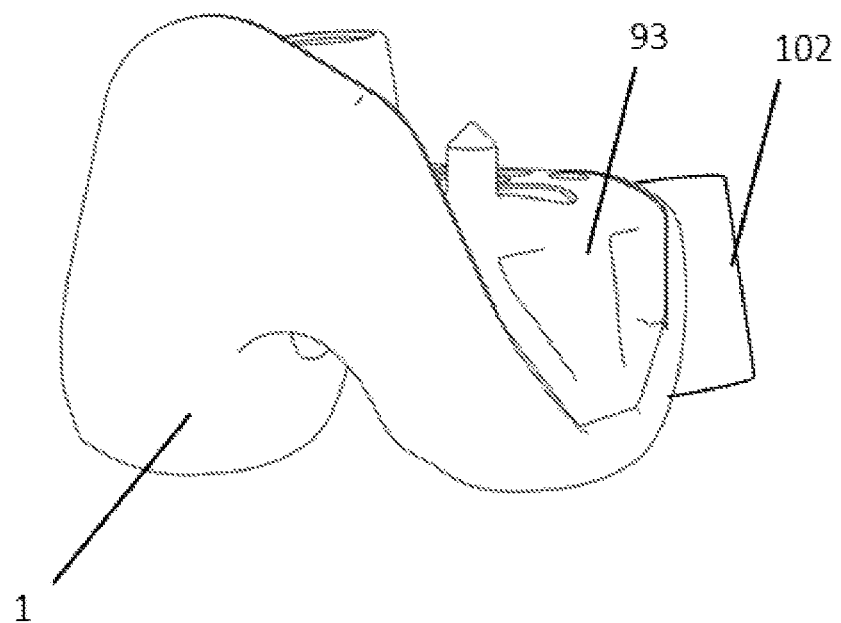
FIG. 24 is a perspective view of a DFR femoral augment assembled onto a femoral component, in accordance with embodiments.
Figure 25:
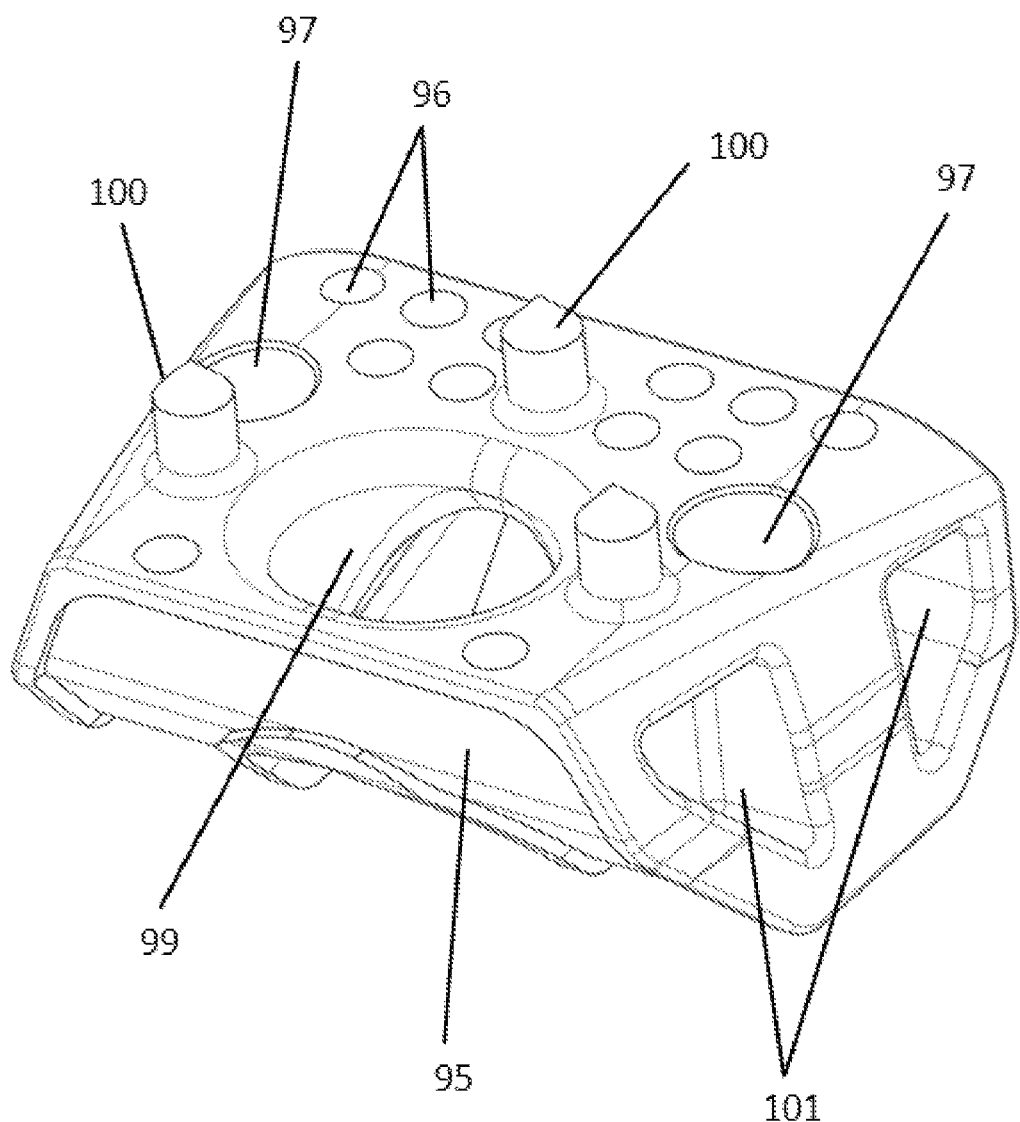
FIG. 25 is a perspective view of a DFR femoral augment, in accordance with embodiments.

FIG. 24 shows a perspective view of a DFR femoral augment 93 assembled onto a femoral component 1. FIG. 25 shows a perspective view of a DFR femoral augment 93 without the femoral component 1, The DFR augment 93 may be placed over the pre-assembled femoral component 1 and may comprise a uniform part. In some embodiments, the DFR augment 93 may comprise a non-uniform part made of a biocompatible metal as described herein. By providing a DFR augment 93, the system may avoid stacking multiple femoral augments 90 on either side of the inter-condylar box 15. Connection techniques known in the art can be used to join the two components such as cement, screws, a snapping feature, or a combination of features, including others that will be understood by one of ordinary skill in the art based on the teachings herein. In the preferred embodiment, the DFR augment 93 can be fixed to the femoral component 1 with cement, screws, or a combination thereof. The DFR augment 93 may comprise one or more pockets 95 along its distal surface that can hold cement in the space between the augment 93 and the femoral component 1 when the augment is placed thereon. The proximal surface of the DFR augment 93 may also comprise one or more features that hold cement as described herein. For example, one or more circular notches 96 may be disposed along the entire proximal surface. Other possible embodiments may include other shaped notches or pockets that follow the shape of the proximal profile. In a preferred embodiment, there are through holes 97 on either side of the DFR augments 93 that allow for screws (such as screws 98 shown in FIG. 26) to be threaded in. The DFR augment 93 may comprise a through hole 99 configured to allow the stem connection 17 of the femoral component 1 to fit therethrough without impingement. Pointed extrusions 100 on the proximal surface of the DFR augment 93 may provide rotational stability of the assembly when implanted. In a preferred embodiment, there may be three extrusions 100 placed circumferentially around the stem connection aperture 99, however more could be placed in similar locations along the same surface as will be understood by one of ordinary skill in the art. The DFR augment 93 may comprise one or more pockets 101 on the medial and/or lateral surfaces to reduce weight. These pockets 101 can come in various shapes and depths as long as they do not interfere with the strength integrity of the component or interfere with the locking features of the component. In the example embodiment shown they are cubic in shape, but it will be understood by one of ordinary skill in the art that they may take more rounded forms. The DFR augment 93 may be symmetric so it can be placed on either right or left femoral components 1 in order to enhance usability and ease of surgical implantation. The DFR augment 93 height can vary to accommodate varying distal resections that range from something larger than a primary distal cut to anything larger, but in a preferred embodiment of the system the DFR augment 93 may comprise a resection height that matches the height of the femoral component condyles 102 as shown in FIG. 24. The size of the DFR augment 93 may correspond to each femoral component 1 size available in the system. In some embodiments, there may be five femoral components 1 as described herein, thus there may also be five DFR augment 93 sizes provided to correspond to each of the femoral components 1. An appropriately-sized DFR augment 93 may be attached to the femoral component 1 on the surgical table before the femoral component 1 is implanted into the patient. The rest of the surgical procedure may follow the same protocol as described above since the same components are still used.

In some embodiments, the DFR augment 93 may comprise a uniform part in order to decrease the number of components a surgeon needs to handle and/or to enhance ease of use.

In some embodiments, the DFR augment 93 may be made of a biocompatible metal. For example, the DFR augment 93 may comprise cobalt chromium, titanium, titanium-based alloys, stainless steel, or the like, or any combination thereof.

Figure 26:
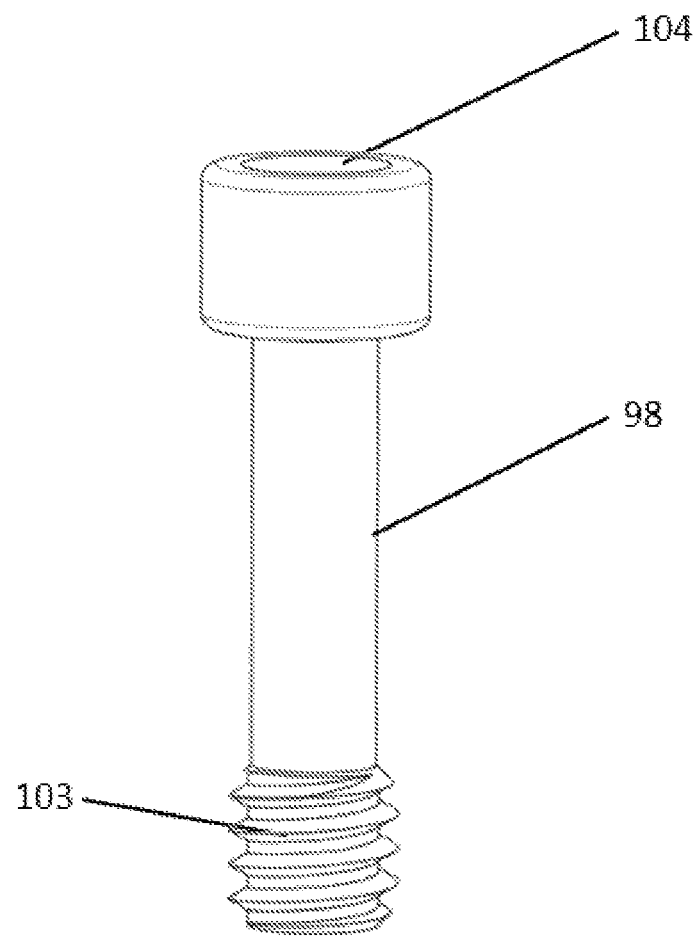
FIG. 26 is a perspective view of a DFR femoral augment screw, in accordance with embodiments.

FIG. 26 shows a perspective view of a DFR augment screw 98. The DFR augment screw 98 may comprise threads 103 on its proximal end that are compatible to the ones found on the proximal aperture 20 of the femoral component 1 in order to facilitate coupling of the screw 98 to the femoral component 1. The head 104 of the DFR augment screw 98 may comprise one or more features compatible (e.g., correspondingly-shaped) to a driver such as a hex or torx driver. In a preferred embodiment, the head 104 may be configured for a hex driver.

In some embodiments, the DFR augment screws 98 may be packaged with the DFR augment 93. In some embodiments, the DFR augment screws 98 may be come pre-assembled onto the DFR augment 93. By packaging the screws 98 and augment 93 together, either pre-assembled or not, use and assembly of the system may be made substantially easier than other systems currently available.

The DFR augment screw 98 may be coupled to the augment 93 using any technique known to one of ordinary skill in the art, such as retaining threads similar to the ones described with respect to the insert 3.

The DFR augment screw 98 may be made of an appropriate biocompatible metal. For example, the DFR augment screw 98 may comprise cobalt chromium, titanium, titanium-based alloys, stainless steel, or the like, or any combination thereof.

Figure 27:
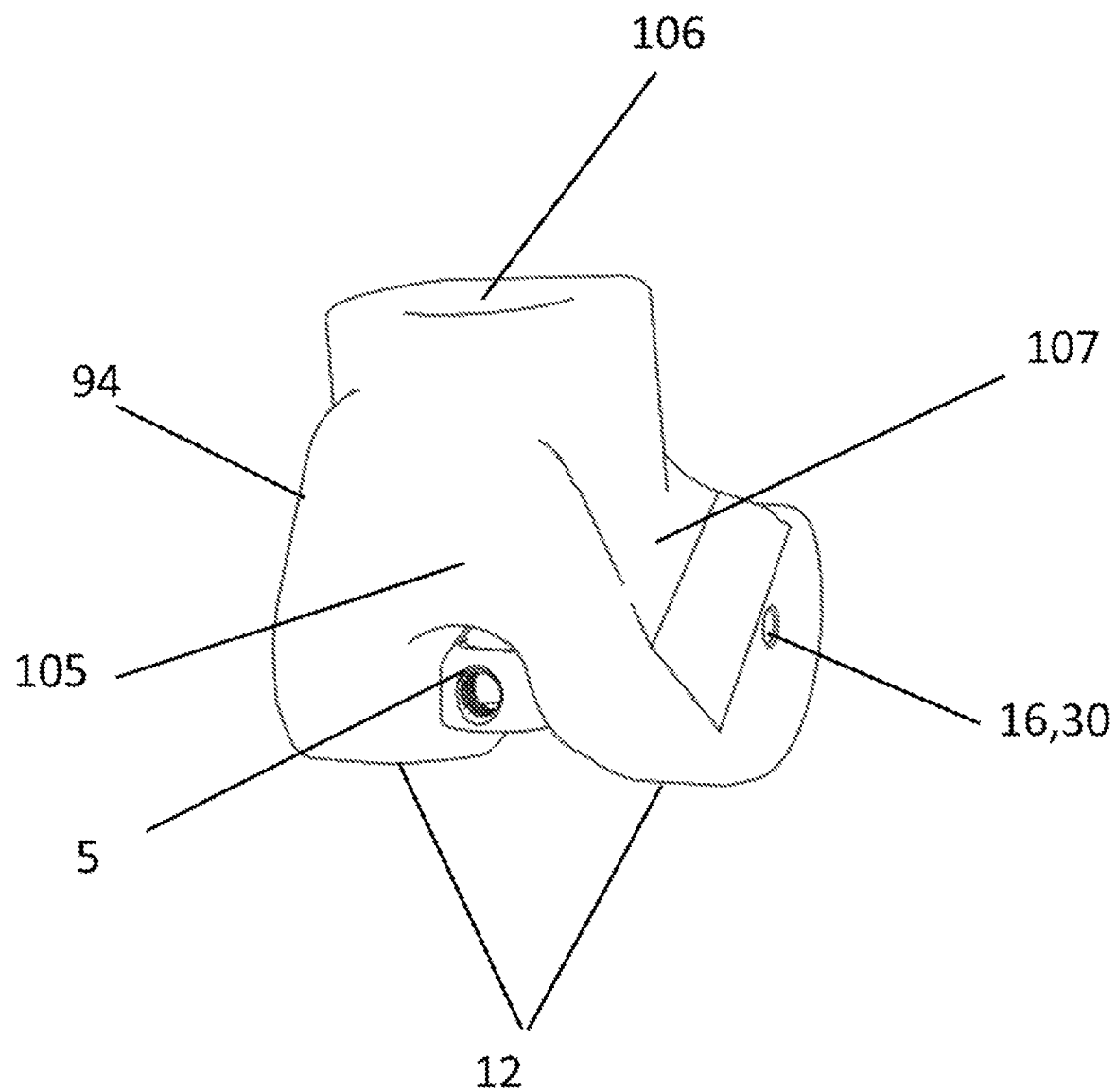
FIG. 27 is a perspective view of a DFR femoral component, in accordance with embodiments.

FIG. 27 is a perspective view of a DFR femoral component 94 which may be utilized instead of femoral component 1 in the hinge knee system in a substantially similar manner. In some instances, for example for distal femoral resections larger than the height provided by the DFR augment 93, a dedicated DFR femoral component 94 may be provided instead of the femoral component 1. The DFR femoral component 94 may be used in cases where neither stacking of the femoral augments 90 nor the DFR augment 93 can replace the amount of distal bone resected from the patient.

The DFR femoral component 94 may come in right and left options and be nearly identical to the femoral component 1 described herein. For example, an anterior flange 105, the condylar bearing surface 12, the intercondylar box 15, and other features of the femoral component 1 may be incorporated into the DFR femoral component 94. The DFR femoral component 94 may also comprise an aperture 106 on the proximal end of the component that allows for a stem connection to be added as described herein. The stem connection aperture 106 may be positioned and oriented similar to other systems in the art. In this particular embodiment, the stem connection features 106 may be made at a 5 degree angle from a vertical plane. This angle may typically be about 5 degrees or about 6 degrees as in other systems known in the art. The main difference between the DFR femoral component 94 and the femoral component 1 may be the material buildup 107 on the distal plane configured to fill the space where the chamfer cuts typically are on primary and revision femoral components. The material buildup 107 may follow the general shape of other DFR femoral components in the art that imitate the anatomical shape of the femur and are no wider than the medial/lateral dimensions of the femoral component 1 described herein. The DFR femoral component 94, similar to the femoral component 1, may come pre-assembled with the hinge components (e.g., hinge box 5, bushings 6, and cross-pin 7) so the same surgical procedure outlined herein with respect to the femoral component 1 may be used when this DFR femoral component 94 is needed. The only difference may be the amount of distal femur resected and the size and/or shape of the optional stems that attach to the stem connection 106 on the DFR femoral component 94.

The DFR femoral component 94 may comprise a single component. The DFR femoral component 94 may comprise a multi-part construction.

The DFR femoral component 94 may comprise a biocompatible material. The DFR femoral component 94 may comprise a biocompatible metal. For example, the DFR femoral component 94 may comprise cobalt chromium, titanium, titanium-based alloys, stainless steel, or the like, or any combination thereof.

Figure 28:
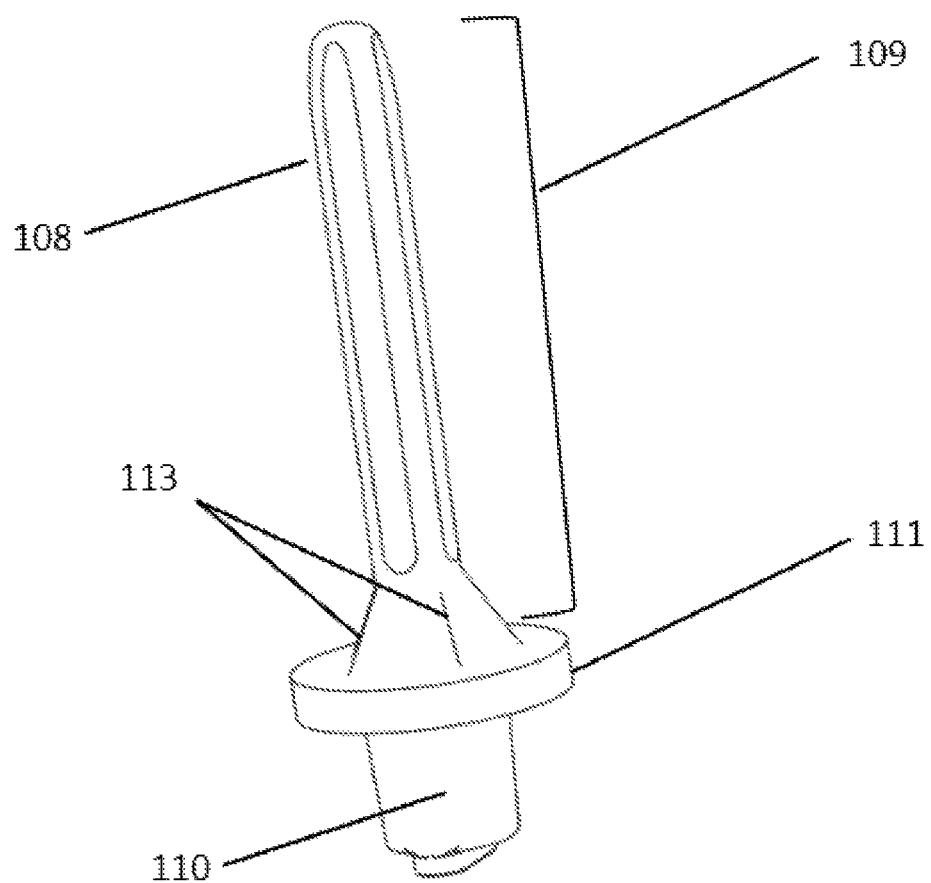
FIG. 28 is a perspective view of a DFR stem extension, in accordance with embodiments.

FIG. 28 shows a perspective view of an exemplary embodiment of a DFR stem extension 108. The proximal end 109 of the stem extension may be similar to other cemented stems known in the art and may be cemented in the medullary canal. The proximal end 109 may comprise one or more connection features 110 configured to attach to the stem connection features 106 on the DFR femoral component 94. The connection feature 110 can be anything known in the art, such as a taper, which is most typically used in similar systems and may also include a screw. Connection methods between the DFR stem 108 and the DFR femoral component 94 may be similar to the connection between the stem extension 112 and the femoral component 1 described herein (e.g., in FIG. 13). In some embodiments, a stem extension 112 may not connect to or be implanted with the DFR femoral component 94 and the DFR stem 108 may not connect to or be implanted with the femoral component 1. For example, there may be slight differences in geometry between the connection feature 110 of the DFR stem 108 and the one found on the stem extension 112 which prevent such mixed connections. The connection feature 110 of the DFR stem may be configured with a larger diameter and a longer taper length, for example, because there may be higher loads at that joint due to the location of the resection and the amount of bone present compared to the joint between the femoral component 1 and the stem connection 112.

In some embodiments, a flange 111 may be disposed towards the distal end of the DFR stem extension 108. Ridges 113 may be disposed circumferentially on the flange 111 to help prevent rotation of the system once it is implanted. The flange 111 may be configured to sit on the resected distal femur when installed in the patient so that there is sufficient contact area between the resected distal femur of the patient and the implants. In at least some instances, it may be important to have the flange 111 in place due to the unique cross-sections that may be encountered at high resection lengths on a femur so that the DFR stem 108 does not fall through and into the medullary canal.

Figure 29:
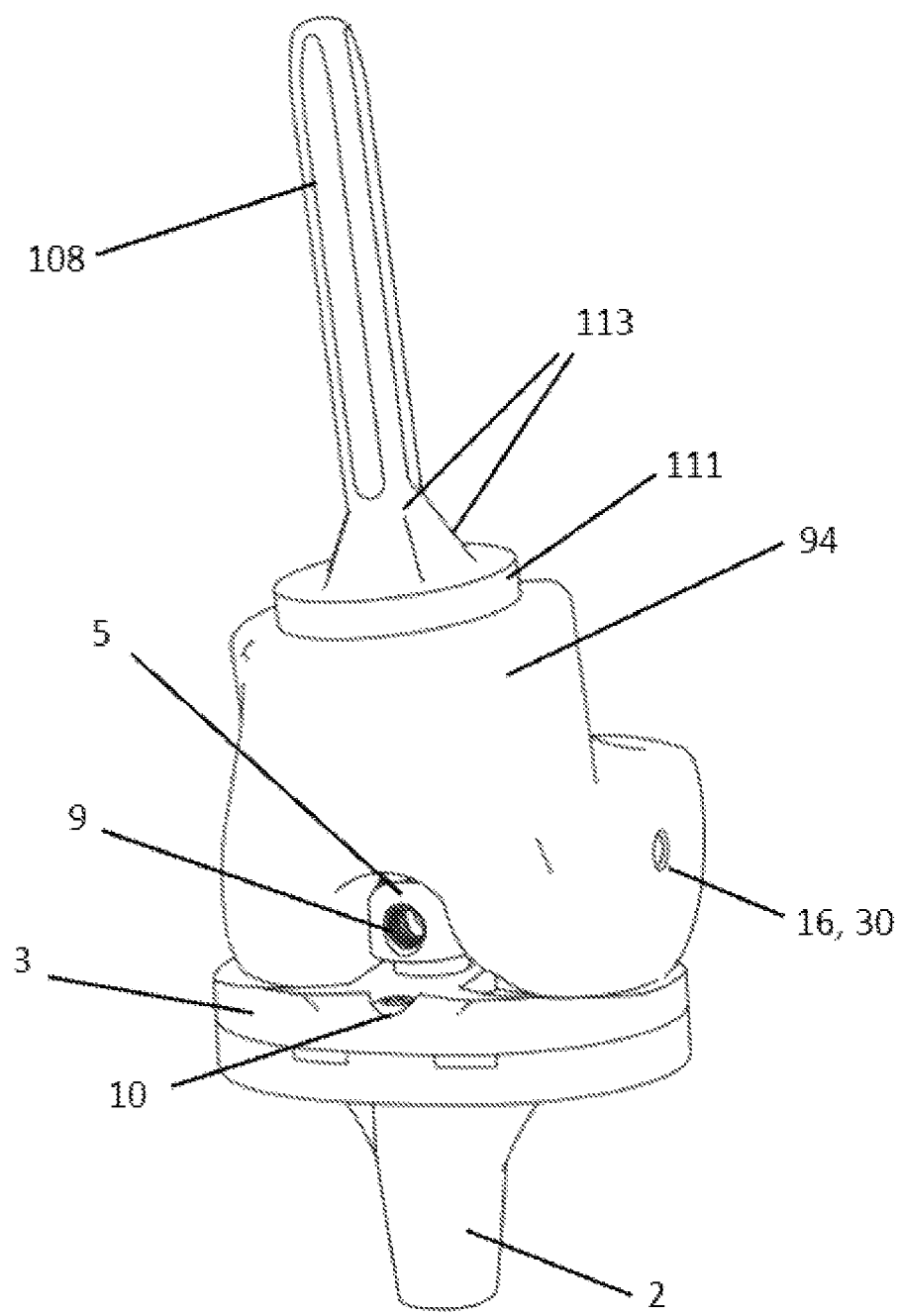
FIG. 29 is a perspective view of an assembled hinge knee system with a DFR femoral component and a DFR stem, in accordance with embodiments.

FIG. 29 depicts the DFR femoral component 94 assembled with the DFR stem extension 108 and other hinge knee components including a tibial tray 2, an insert 3, a tibial bushing 4, a hinge box 5, two bushings 6, a cross-pin 7, a hinge post assembly 8, a hinge post set screw 9, and a poly locking screw 10, which may be substantially similar to those described herein and may be coupled to the DFR femoral component 94 in a substantially similar manner to that described herein with respect to femoral component 1.

Figure 30:
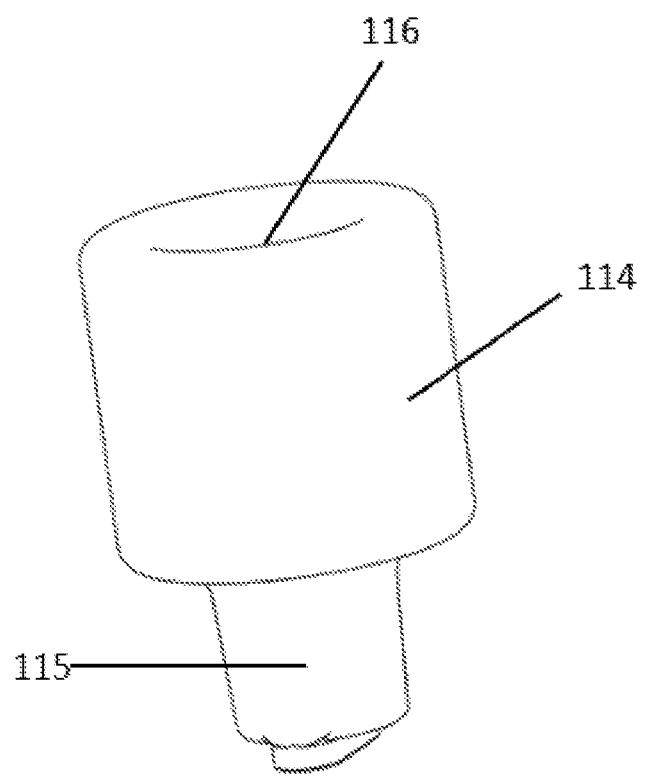
FIG. 30 is a perspective view of a DFR stem collar, in accordance with embodiments.

FIG. 30 shows a perspective view of a DFR stem collar 114. The DFR stem collar 114 may be cylindrical in shape, but can take on any cross-sectional geometry as long as the function and strength of the component is maintained as described herein. A preferred embodiment of the DFR stem collar 114 may comprise of a cylindrical cross-section configured to most closely match the geometry of the proximal end of the DFR femoral component 94 and the shape of the flange 111 of the DFR stem 108.

The DFR stem collar 114 may comprise a single uniform component. The DFR stem collar 114 may comprise a multi-part construction.

The DFR stem collar 114 may comprise a biocompatible material. The DFR stem collar 114 may comprise a biocompatible metal. For example, the stem collar 114 may comprise cobalt chromium, titanium, titanium-based alloys, stainless steel, or the like, or any combination thereof.

Figure 31:
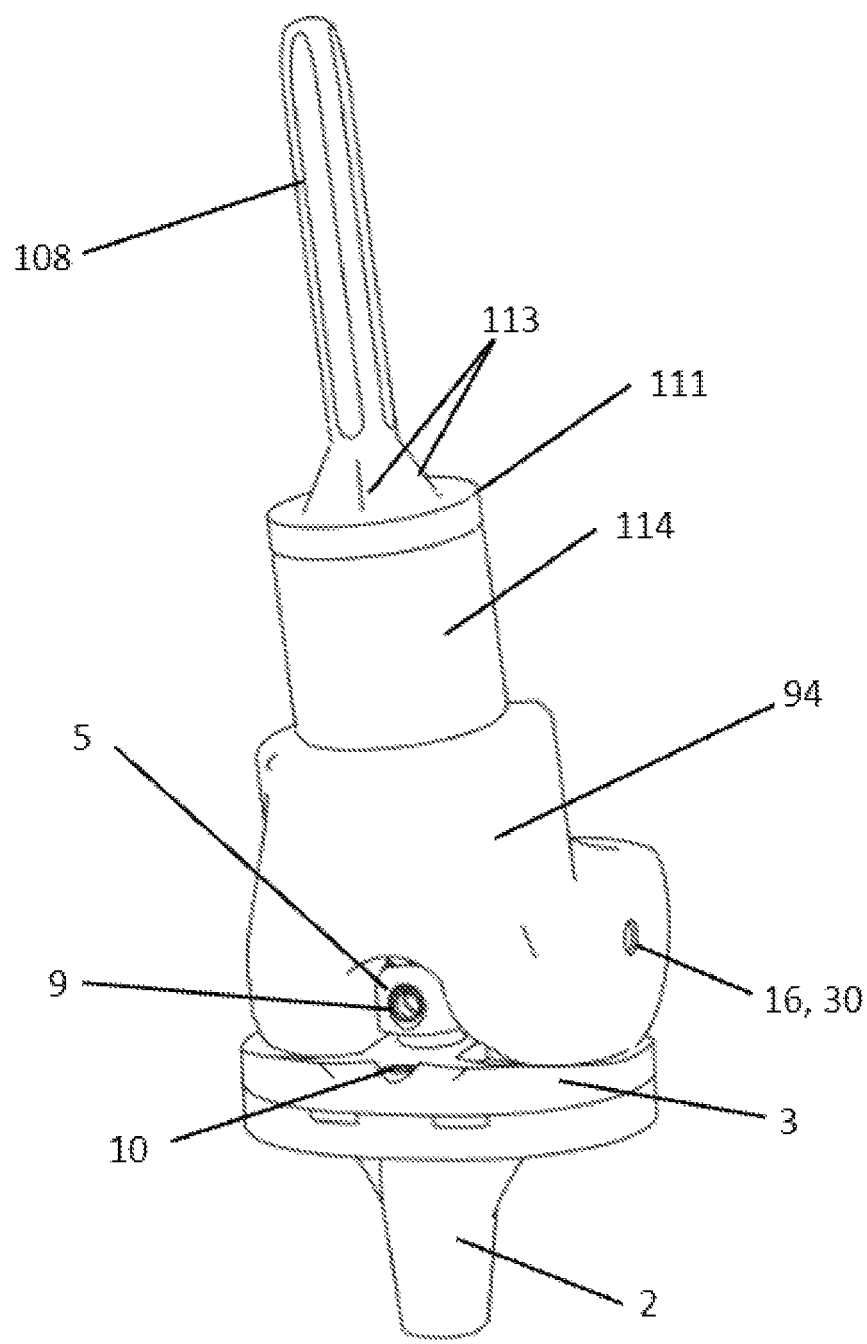
FIG. 31 is a perspective view of an assembled hinge knee system with a DFR femoral component, a DFR stem, and a DFR stem collar, in accordance with embodiments.

FIG. 31 shows a perspective view of an assembled hinge knee system with a DFR femoral component 94, a DFR stem 108, and a DFR stem collar 114. A DFR stem collar 114 may be implanted between the DFR femoral component 94 and the DFR stem 108 in order to allow a surgeon to use the system described herein for distal femoral resections that are larger than the height of the DFR femoral component 94 itself. The resected bone and joint space needs to be properly replaced to allow for proper range of motion of the patient so there are various lengths of DFR stem collar 114 provided in the system. The DFR stem collar 114 may be provided in the same cross-sectional dimensions as flange 111, in this case with the same diameter, but may be provided in various lengths. The lengths may range from something as small as about 5 mm to about 20 mm and may, for example, be provided in 5 mm jumps. In a preferred embodiment, the system may provide two different lengths of DFR stem collars 114 for the user to choose from.

Figure 32:
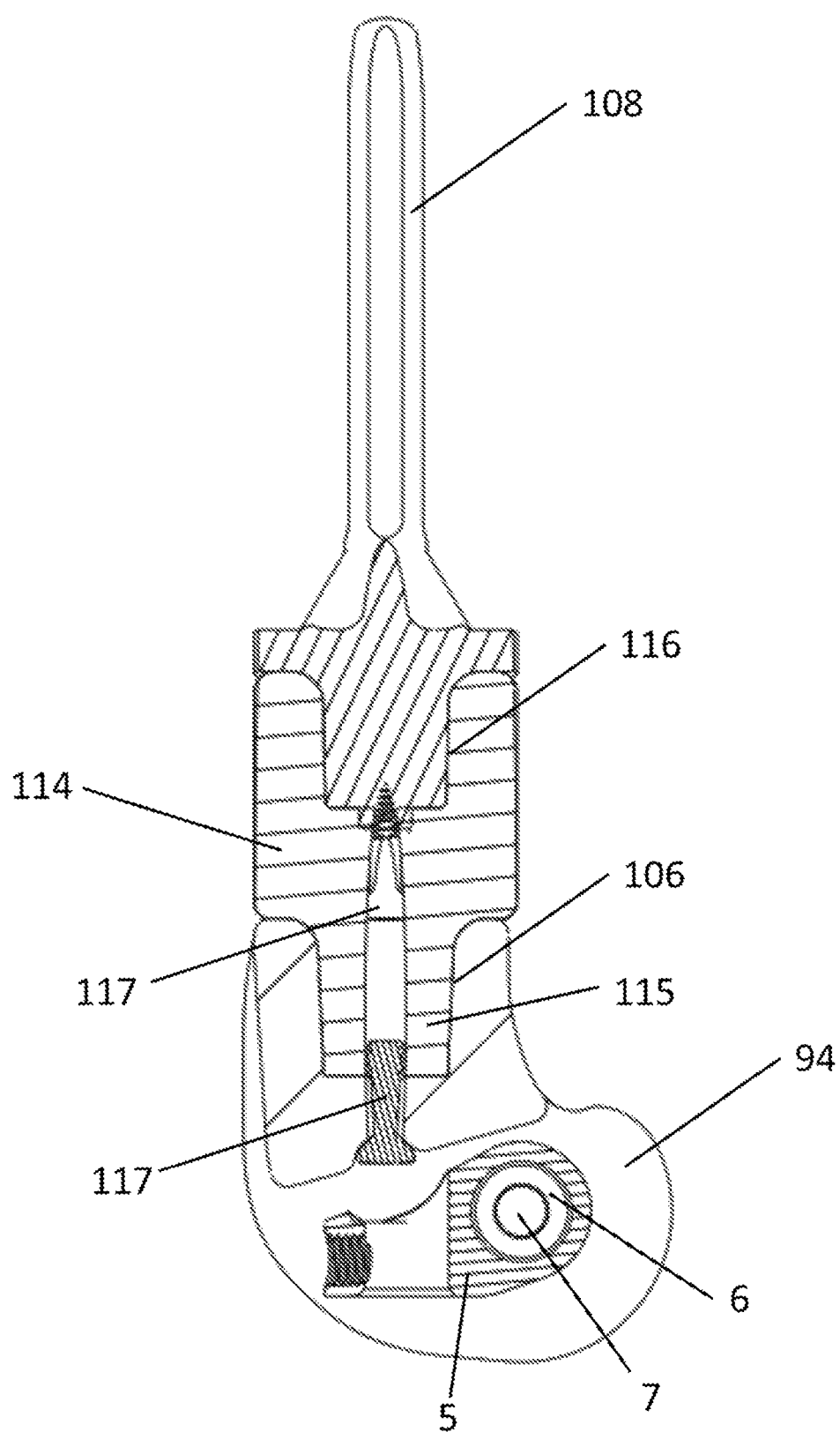
FIG. 32 is a lateral cross-sectional view of a DFR stem collar, in accordance with embodiments.

FIG. 32 is a lateral cross-sectional view of a DFR stem collar 114 disposed between a femoral component 94 and a DFR stem 108. A connection feature 115 may be disposed on the distal end of the DFR stem collar 114 that matches the geometry of the connection features 110 of the DFR stem 108. The connection feature 115 may be configured to engage with and connect to the DFR femoral component 94 in the same manner described herein with respect to the DFR stem 108 to the stem connection feature 106 of the DFR femoral component 94. A proximal aperture 116 may be disposed on the DFR stem collar 114 which corresponds to the geometry of the stem connection feature 106 of the DFR femoral component 94. The aperture 116 may match the stem connection feature 106 because the DFR stem 108 may also connect to aperture 116 in the same manner described herein with respect to the DFR stem 108 connection to aperture 106 of the DFR femoral component 96. There may be one or more feature inside the DFR stem collar 114, such as a threaded aperture as shown in FIG. 32 that may allow for a screw 117 to be used to connect the respective components together, similar to the connection method between the DFR stem 108 and the DFR femoral component 94 described herein. For example, screw 117 may be configured to couple the DFR stem 108 to the DFR femoral component 94, the DFR stem 108 to the DFR stem collar 114, and/or the DFR stem collar 114 to the DFR femoral component 94.

Figure 33:
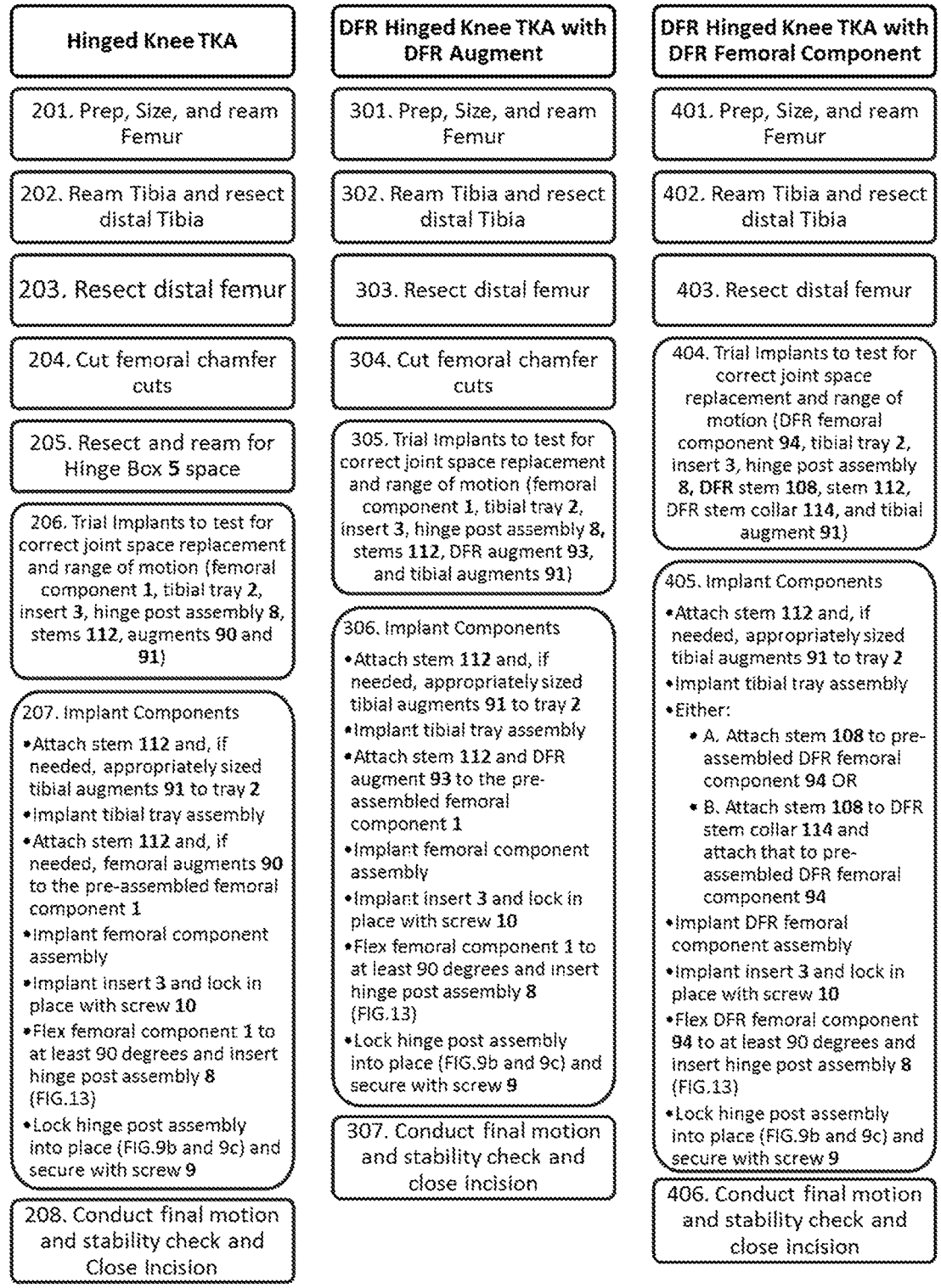
FIG. 33 shows flowcharts of various methods of implanting a hinge knee system if the patient is undergoing a primary surgery (e.g., the patient has not had any previous knee surgeries), in accordance with embodiments.

FIG. 33 shows flowcharts of various methods of implanting a hinge knee system if the patient is undergoing a primary surgery (e.g., the patient has not had any previous knee surgeries). The left-most method describes a hinged knee total knee arthroplasty (TKA). The middle method describes a DFR hinged knee TKA with use of a DFR augment. The right-most method describes a DFR hinged knee TKA with use of a DFR femoral component.

In the hinged knee TKA method shown on the left, Step 201 may comprise preparing, sizing, and reaming the femur.

Step 202 may comprise reaming the tibia and/or resecting the distal tibia.

Step 203 may comprise resecting the distal femur.

Step 204 may comprise cutting one or more femoral chamfer cuts.

Step 205 may comprise resecting and/or reaming space for a hinge box (e.g., hinge box 5 described herein).

Step 206 may comprise testing one or more trial implants for the correct joint space replacement and/or desired range of motion. Step 6 may optionally comprise testing one or more femoral components 1, one or more tibial trays 2, one or more inserts 3, one or more hinge post assemblies 8, one or more stems 112, one or more femoral augments 90, and/or one or more tibial augments 91.

Step 207 may comprise implanting the components of the hinged knee system. Step 7 may comprise one or more sub-steps. For example, Step 7 may comprise (a) attaching optional stem 112 and optional tibial augments 91 to tibial tray 2, (b) implanting the tibial tray 2 assembly, (c) attaching optional stem 112 and optional femoral augments 90 to the pre-assembled femoral component 1, (d) implanting the femoral component 1 assembly, (e) implanting insert 3, (f) locking insert 3 in place with screw 10, (g) flexing the femoral component 1 to at least 90 degrees and inserting the hinge post assembly 8 (e.g., as shown in FIG. 13), (h) locking the hinge post assembly 8 into place, and/or (i) securing the hinge post assembly 9 with screw 9.

Step 208 may comprise conducting final motion and stability checks before closing the incision.

Although the steps above show a method of performing a hinged knee TKA using the system described herein, a person of ordinary skill in the art will recognize many variations based on the teaching described herein. The steps may be completed in a different order. Steps may be added or deleted. Some of the steps may comprise sub-steps. Many of the steps may be repeated as often as necessary ensure correct placement of one or more article component on the operator-side of the first platform.

For example, in many embodiments, augments 90, 91 are not utilized, stem 112 is attached only to the femur or tibia but not both, stem 112 is not necessary at all, and/or other mechanisms for securing components to one another may be utilized.

In the DFR hinged knee TKA with DFR augment method shown in the middle, Step 301 may comprise preparing, sizing, and reaming the femur.

Step 302 may comprise reaming the tibia and/or resecting the distal tibia.

Step 303 may comprise resecting the distal femur.

Step 304 may comprise cutting one or more femoral chamfer cuts.

Step 305 may comprise testing one or more trial implants for the correct joint space replacement and/or desired range of motion. Step 6 may optionally comprise testing one or more femoral components 1, one or more tibial trays 2, one or more inserts 3, one or more hinge post assemblies 8, one or more stems 112, one or more DFR augments 93, and/or one or more tibial augments 91.

Step 306 may comprise implanting the components of the DFR hinged knee system. Step 6 may comprise one or more sub-steps. For example, Step 6 may comprise (a) attaching optional stem 112 and optional tibial augments 91 to tibial tray 2, (b) implanting the tibial tray 2 assembly, (c) attaching optional stem 112 and DFR femoral augments 93 to the pre-assembled femoral component 1, (d) implanting the femoral component 1 assembly, (e) implanting insert 3, (f) locking insert 3 in place with screw 10, (g) flexing the femoral component 1 to at least 90 degrees and inserting the hinge post assembly 8 (e.g., as shown in FIG. 13), (h) locking the hinge post assembly 8 into place, and/or (i) securing the hinge post assembly 9 with screw 9.

Step 307 may comprise conducting final motion and stability checks before closing the incision.

Although the steps above show a method of performing a DFR hinged knee TKA using the DFR augment system described herein, a person of ordinary skill in the art will recognize many variations based on the teaching described herein. The steps may be completed in a different order. Steps may be added or deleted. Some of the steps may comprise sub-steps. Many of the steps may be repeated as often as necessary ensure correct placement of one or more article component on the operator-side of the first platform.

For example, in many embodiments, augments 91 are not utilized, stem 112 is attached only to the femur or tibia but not both, stem 112 is not necessary at all, and/or other mechanisms for securing components to one another may be utilized.

In the DFR hinged knee TKA with DFR femoral component method shown on the right, Step 401 may comprise preparing, sizing, and reaming the femur.

Step 402 may comprise reaming the tibia and/or resecting the distal tibia.

Step 403 may comprise resecting the distal femur.

Step 404 may comprise testing one or more trial implants for the correct joint space replacement and/or desired range of motion. Step 6 may optionally comprise testing one or more DFR femoral components 94, one or more tibial trays 2, one or more inserts 3, one or more hinge post assemblies 8, one or more DFR stems 108, one or more stems 112, one or more DFR stem collars 114, and/or one or more tibial augments 91.

Step 405 may comprise implanting the components of the DFR hinged knee system with DFR femoral component 94. Step 5 may comprise one or more sub-steps. For example, Step 5 may comprise (a) attaching optional stem 112 and optional tibial augments 91 to tibial tray 2, (b) implanting the tibial tray 2 assembly, (c) attaching DFR stem 108 to the pre-assembled DFR femoral component 94, (d) attaching DFR stem 108 to the DFR stem collar 114 and attaching the DFR stem-DFR stem collar complex to the pre-assembled DFR femoral component 94, (e) implanting the DFR femoral component 94 assembly, (f) implanting insert 3, (g) locking insert 3 in place with screw 10, (h) flexing the DFR femoral component 94 to at least 90 degrees and inserting the hinge post assembly 8 (e.g., as shown in FIG. 13), (i) locking the hinge post assembly 8 into place, and/or (j) securing the hinge post assembly 9 with screw 9.

Step 406 may comprise conducting final motion and stability checks before closing the incision.

Although the steps above show a method of performing a DFR hinged knee TKA using the DFR femoral component system described herein, a person of ordinary skill in the art will recognize many variations based on the teaching described herein. The steps may be completed in a different order. Steps may be added or deleted. Some of the steps may comprise sub-steps. Many of the steps may be repeated as often as necessary ensure correct placement of one or more article component on the operator-side of the first platform.

For example, in many embodiments, augments 91 are not utilized, stem 112 and/or stem 108 is not necessary at all, and/or other mechanisms for securing components to one another may be utilized.

The present disclosure describes both preferred embodiments as well as possible alternate embodiments, but it should not be limited to any of the particular forms shown. The disclosure is intended to cover any variations or adaptations of the invention that capture the idea behind what was described.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A hinge knee system comprising:
a femoral component;
an insert;
a tibial tray configured to be coupled to the insert;
a tibial bushing configured to be disposed between the tibial tray and the insert;
a poly locking screw configured to secure the tibial tray to the insert;
a hinge box configured to be disposed between the femoral component and the insert;
one or more cross-pin bushings configured to be disposed within the hinge box;
a cross-pin configured to secure the hinge box to the femoral component;
a hinge post configured to couple the hinge box to the tibial tray; and
a hinge post set screw configured to secure the hinge box to the hinge post,
wherein the hinge post set screw comprises threads on a proximal end thereof configured to correspond to threads in an anterior aperture of the hinge box.

2. The hinge knee system of claim 1, wherein the tibial bushing comprises a central aperture configured to accept the hinge post therewithin with a clearance fit.

3. The hinge knee system of claim 1, wherein the hinge box comprises a hinge post through hole adjacent an anterior end thereof.

4. The hinge knee system of claim 3, wherein the hinge post through hole is configured sized and shaped to correspond to an outer dimension of the hinge post.

5. The hinge knee system of claim 1, wherein the hinge post comprises a hinge post body, a hinge post shaft, and a hinge post tab.

6. The hinge knee system of claim 5, wherein the hinge post body, hinge post shaft, and hinge post tab are pre-assembled into a manufactured configuration of a packaged configuration.

7. The hinge knee system of claim 6, wherein the hinge post shaft is configured to be rotated from the packaged configuration to a locked configuration during surgery to fix the femoral component to the tibial tray and insert.

8. The hinge knee system of claim 7, wherein rotation of the hinge post shaft to the locked configuration is configured to translate the hinge post tab such that it extrudes out of the hinge post body into a cut out of the tibial bushing.

9. The hinge knee system of claim 5, wherein the hinge post body comprises a uniform distal diameter shaft and a proximal head comprising an overhang, tab, or pin in the anterior direction.

10. The hinge knee system of claim 9, wherein the overhang is configured to sit on a countersink of an aperture of the hinge box to prevent the hinge post body from falling through the hinge box.

11. The hinge knee system of claim 9, wherein the proximal head may be configured ensure that an anterior aperture on the hinge post body is aligned with a threaded aperture on the hinge box when correctly oriented.

12. The hinge knee system of claim 5, wherein the hinge post body comprises a distal aperture extending therethrough on a distal end thereof.

13. The hinge knee system of claim 12, wherein the distal aperture is configured to hold the hinge post tab.

14. The hinge knee system of claim 5, wherein the hinge post body comprises a central channel extending axially from a proximal head of the hinge post body to a distal aperture of the hinge post body.

15. The hinge knee system of claim 14, wherein the hinge post shaft is configured to be rotatably disposed within the central channel of the hinge post body.

16. The hinge knee system of claim 15, wherein the proximal head comprises a countersink configured to keep the hinge post shaft in place when disposed within the central channel of the hinge post body.

17. The hinge knee system of claim 5, wherein the hinge post shaft comprises a proximal head, a proximal shaft portion below the proximal head, a distal shaft portion below the proximal shaft portion and smaller in diameter than the proximal shaft portion, and a distal feature on a distal end thereof.

18. The hinge knee system of claim 17, wherein the distal feature is configured to be coupled to a corresponding feature on the hinge post tab.

19. The hinge knee system of claim 17, wherein the distal feature comprises a pin or a cylindrical component.

20. The hinge knee system of claim 17, wherein the hinge post shaft comprises an aperture disposed on an anterior side of the proximal shaft portion configured to align with an aperture on the hinge post body when correctly rotationally aligned.

21. The hinge knee system of claim 17, wherein an anterior, proximal end of the proximal head comprises notch cut disposed therein and configured to match a lip feature on the hinge post body to align and orient insertion of the hinge post shaft into a central channel of the hinge post body.

22. The hinge knee system of claim 17, wherein the proximal head of the hinge post shaft comprises a track to guide rotation of the hinge post shaft within a central channel of the hinge post body.

23. The hinge knee system of claim 22, wherein the track comprises one or more indents disposed thereon configured to fit a lip of the hinge post body therein to provide for incremental rotations of the hinge post shaft within the hinge post body.

24. The hinge knee system of claim 23, wherein the hinge post further comprises a hinge post spring configured to keep the lip engaged with the one or more indents until the hinge post shaft is pressed and rotated within the hinge post body.

25. The hinge knee system of claim 5, wherein the hinge post tab is configured to fit within a distal aperture on a distal end of the hinge post body.

26. The hinge knee system of claim 5, wherein the hinge post tab is configured to be fully seated within the hinge post body when disposed within the distal aperture.

27. The hinge knee system of claim 5, wherein the hinge post tab comprises an aperture configured to engage with a distal feature of the hinge post shaft.

28. The hinge knee system of claim 1, wherein the hinge post set screw is configured to be threaded through the anterior aperture of the hinge box and one or more anterior apertures of the hinge post.

29. The hinge knee system of claim 28, wherein the hinge post set screw is configured to lock the hinge post to the hinge box and prevent rotation or disassembly of the hinge post after being secured thereto.

30. A method of anteriorly assembling a hinge knee system, the method comprising:
resecting a tibia of a patient to correspond to a tibial component of a hinge knee system, the tibial component comprising a tibial tray and an insert;
implanting the tibial component into the tibia of the patient;
resecting a femur of the patient to correspond to a femoral component of the hinge knee system;
implanting the femoral component into the femur of the patient; flexing the femoral component to expose a hinge box coupled to the femoral component;
anteriorly assembling a hinge post through the hinge box into the insert;
locking the hinge post to the tibial component; and
securing the hinge post to the hinge box with a hinge post set screw,
wherein the hinge post set screw comprises threads on a proximal end thereof configured to correspond to threads in an anterior aperture of the hinge box.

31. The method of claim 30, wherein locking the hinge post to the tibial component comprises rotating a hinge post shaft relative to a hinge post body of the hinge post in order to translate a hinge post tab disposed within the hinge post shaft such that it extrudes from the hinge post shaft into a tibial bushing of the tibial component.

32. The method of claim 30, wherein the hinge post comprises a hinge post body, a hinge post shaft, and a hinge post tab, wherein the hinge post body, hinge post shaft, and hinge post tab are pre-assembled into a manufactured configuration of a packaged configuration, wherein the hinge post shaft is configured to be rotated from the packaged configuration to a locked configuration during surgery to fix the femoral component to the tibial tray and insert, and wherein rotation of the hinge post shaft to the locked configuration is configured to translate the hinge post tab such that it extrudes out of the hinge post body into a cut out of the tibial bushing.

33. The method of claim 30, wherein the hinge post comprises a hinge post body, a hinge post shaft, and a hinge post tab, and wherein the hinge post body comprises a uniform distal diameter shaft and a proximal head comprising an overhang, tab, or pin in the anterior direction.

34. The method of claim 30, wherein the hinge post comprises a hinge post body, a hinge post shaft, and a hinge post tab, and wherein the hinge post body comprises a central channel extending axially from a proximal head of the hinge post body to a distal aperture of the hinge post body.

35. The hinge knee system of claim 30, wherein the hinge post comprises a hinge post body, a hinge post shaft, and a hinge post tab, and wherein the hinge post tab comprises an aperture configured to engage with a distal feature of the hinge post shaft.

\* \* \* \* \*

UNITED STATES PATENT AND TRADEMARK OFFICE
CERTIFICATE OF CORRECTION

PATENT NO. : 11,051,948 B2
APPLICATION NO. : 16/399762
DATED : July 6, 2021
INVENTOR(S) : Arnold et al.

Page 1 of 1

It is certified that error appears in the above-identified patent and that said Letters Patent is hereby corrected as shown below:

In the Claims

Column 34, Lines 37-38, delete "a poly locking screw configured to secure the tibial tray to the insert;"

Column 34, Lines 41-42, delete "one or more cross-pin bushings configured to be disposed within the hinge box;"

Column 34, Lines 43-44, delete "a cross-pin configured to secure the hinge box to the femoral component;"

Signed and Sealed this
Second Day of August, 2022

Katherine Kelly Vidal
*Director of the United States Patent and Trademark Office*